(12) United States Patent
Follmann et al.

(10) Patent No.: US 9,133,191 B2
(45) Date of Patent: Sep. 15, 2015

(54) SUBSTITUTED TRIAZINE DERIVATIVES AND USE THEREOF AS STIMULATORS OF SOLUBLE GUANYLATE CYCLASE

(71) Applicant: Bayer Intellectual Property GmbH, Monheim (DE)

(72) Inventors: Markus Follmann, Köln (DE); Johannes-Peter Stasch, Solingen (DE); Gorden Redlich, Bochum (DE); Nils Griebenow, Dormagen (DE); Frank Wunder, Wuppertal (DE); Dieter Lang, Velbert (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/371,054

(22) PCT Filed: Jan. 8, 2013

(86) PCT No.: PCT/EP2013/050179
§ 371 (c)(1),
(2) Date: Jul. 8, 2014

(87) PCT Pub. No.: WO2013/104597
PCT Pub. Date: Jul. 18, 2013

(65) Prior Publication Data
US 2015/0094308 A1    Apr. 2, 2015

(30) Foreign Application Priority Data
Jan. 11, 2012  (DE) .................... 10 2012 200 360

(51) Int. Cl.
*C07D 471/04*  (2006.01)
*A61K 31/53*  (2006.01)
*A61K 45/06*  (2006.01)

(52) U.S. Cl.
CPC .............. *C07D 471/04* (2013.01); *A61K 31/53* (2013.01); *A61K 45/06* (2013.01)

(58) Field of Classification Search
CPC ............................ C07D 471/04; A61K 31/53
USPC ......................................... 514/242; 544/182
See application file for complete search history.

(56) References Cited

U.S. PATENT DOCUMENTS

| 5,976,523 | A  | 11/1999 | Awaya et al. |
| 6,166,027 | A  | 12/2000 | Straub et al. |
| 6,180,656 | B1 | 1/2001  | Furstner et al. |
| 6,451,805 | B1 | 9/2002  | Straub et al. |
| 6,743,798 | B1 | 6/2004  | Straub et al. |
| 6,833,364 | B1 | 12/2004 | Straub et al. |
| 6,903,089 | B1 | 6/2005  | Stasch et al. |
| 7,173,037 | B2 | 2/2007  | Alonso-Alija et al. |
| 7,410,973 | B2 | 8/2008  | Feurer et al. |
| 7,414,136 | B2 | 8/2008  | Matsumura et al. |
| 7,541,367 | B2 | 6/2009  | Chiu et al. |
| 8,058,282 | B2 | 11/2011 | Adams et al. |
| 8,242,272 | B2 | 8/2012  | Jimenez et al. |
| 8,309,551 | B2 | 11/2012 | Schirok et al. |
| 8,420,656 | B2 | 4/2013  | Follmann et al. |
| 2004/0235863 | A1 | 11/2004 | Feurer et al. |
| 2006/0014951 | A1 | 1/2006  | Feurer et al. |
| 2006/0052309 | A1 | 3/2006  | Alonso-Alija et al. |
| 2008/0004257 | A1 | 1/2008  | Chan et al. |
| 2010/0298336 | A1 | 11/2010 | Attardo et al. |
| 2011/0218202 | A1 | 9/2011  | Brockunier et al. |
| 2012/0029002 | A1 | 2/2012  | Straub et al. |
| 2013/0072492 | A1 | 3/2013  | Raghavan et al. |
| 2013/0172372 | A1 | 7/2013  | Follmann et al. |
| 2013/0178475 | A1 | 7/2013  | Moore et al. |
| 2013/0210824 | A1 | 8/2013  | Follmann et al. |
| 2013/0338137 | A1 | 12/2013 | Follmann et al. |
| 2014/0100229 | A1 | 4/2014  | Follmann et al. |
| 2014/0148433 | A1 | 5/2014  | Follmann et al. |
| 2014/0171434 | A1 | 6/2014  | Follmann et al. |
| 2014/0228366 | A1 | 8/2014  | Follmann et al. |
| 2014/0249168 | A1 | 9/2014  | Follmann et al. |
| 2014/0350020 | A1* | 11/2014 | Follmann et al. ............. 514/243 |
| 2014/0357637 | A1 | 12/2014 | Follmann et al. |
| 2015/0025090 | A1 | 1/2015  | Follmann et al. |

FOREIGN PATENT DOCUMENTS

| CA | 2804470 A1 | 1/2012 |
| CA | 2809911 A1 | 3/2012 |
| CA | 2834901 A1 | 11/2012 |
| CA | 2840886 A1 | 1/2013 |
| CN | 1613849 A  | 5/2005 |
| EP | 0 634 413 A1 | 1/1995 |
| WO | 98/16223 A1 | 4/1998 |

(Continued)

OTHER PUBLICATIONS

Badesch et al., "Prostanoid Therapy for Pulmonary Arterial Hypertension," Journal of the American College of Cardiology, (Jun. 16, 2004), vol. 43, No. 12 Suppl S, pp. 56s-61s.

Banholzer et al., "277. Zum Mechanismus der Thermischen Decarbonylierung von Oxalessigestern," Helvetica Chimica Acta, (1959), vol. 42, No. 277, pp. 2584-2597.

Becker et al., "NO-independent regulatory site of direct sGC stimulators like YC-1 and BAY 41-2272," BMC Pharmacology, (Dec. 28, 2001), vol. 1, No. 13, pp. 1-12.

Cheng et al., "Potential Purine Antagonists VII. Synthesis of 6-Alkylpyrazolo-[3,4-d]pyrimidines," The Journal of Organic Chemistry, (Feb. 1958), vol. 23, No. 2, pp. 191-200.

(Continued)

*Primary Examiner* — Kahsay Habte
(74) *Attorney, Agent, or Firm* — Buchanan Ingersoll & Rooney PC

(57) ABSTRACT

The present application relates to novel substituted fused pyrimidines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

7 Claims, No Drawings

(56) References Cited

FOREIGN PATENT DOCUMENTS

| WO | 00/06568 A1 | 2/2000 |
|---|---|---|
| WO | 00/06569 A1 | 2/2000 |
| WO | 01/83490 A1 | 11/2001 |
| WO | 02/059083 A2 | 8/2002 |
| WO | 03/095451 A1 | 11/2003 |
| WO | 2004/009590 A1 | 1/2004 |
| WO | 2005/073234 A2 | 8/2005 |
| WO | 2006/081230 A2 | 8/2006 |
| WO | 2009/145814 A2 | 12/2009 |
| WO | 2010/065275 A2 | 6/2010 |
| WO | 2011/115804 A1 | 9/2011 |
| WO | 2011/149921 A1 | 12/2011 |
| WO | 2011/161099 A1 | 12/2011 |
| WO | 2013/030138 A1 | 3/2013 |

OTHER PUBLICATIONS

Daley et al., "The First Complete Identification of a Diastereomeric Catalyst-Substrate (Alkoxide) Species in an Enantioselective Ketone Hydrogenation. Mechanistic Investigations," Journal of the American Chemical Society, (Mar. 16, 2002), vol. 124, No. 14, pp. 3680-3691.

Evgenov et al., "NO-independent stimulators and activators of soluble guanylate cyclase: discovery and therapeutic potential," Nature Reviews Drug Discovery, (Sep. 2006), vol. 5, No. 9, pp. 755-768.

Glass et al., "Stimulation of Human Platelet Guanylate Cyclase by Fatty Acids," The Journal of Biological Chemistry, (Feb. 25, 1977), vol. 252, No. 4, pp. 1279-1285.

Greene et al., "The Role of Protective Groups in Organic Synthesis," Greene's Protective Groups in Organic Synthesis, Fourth Edition, (2007), pp. 1-15.

Ghofrani et al., "Soluble Guanylate Cyclase Stimulation: An Emerging Option in Pulmonary Hypertension Therapy," European Respiratory Review, (2009), vol. 18, No. 11, pp. 35-41.

Grassetti et al., "Synthesis of Some Homologs of Fluoropyruvic Acid and Their Effect on the Carbohydrate Metabolism of Ehrlich Ascites Tumor and on Lactate Dehydrogenase," J. Med. Chem., (Jan. 1966), vol. 9, No. 1, pp. 149-151.

Hassan et al., "Aryl-Aryl Bond Formation One Century after the Discovery of the Ullmann Reaction," Chemical Reviews, (Mar. 8, 2002), vol. 102, No. 5, pp. 1359-1470.

Herdemann et al., "Identification of Potent ITK Inhibitors Through Focused Compound Library Design Including Structural Information," Bioorganic & Medicinal Chemistry Letters, (Dec. 1, 2010), vol. 20, No. 23, pp. 6998-7003.

Hughes, "Progress in the Mitsunobu Reaction. A Review," Organic Preparations and Procedures Int., (1996), vol. 28, No. 2, pp. 127-164.

Kelley et al., "Synthesis and Anticonvulsant Activity of N-Benzylpyrrolo[2,3-d]-, -pyrazolo[3,4-d]-, and -triazolo[4,5-d] pyrimidines: Imidazole Ring-Modified Analogues of 9-(2-Fluorobenzyl)-6-(methylamino)-9H-purin," Journal of Medicinal Chemistry, (Sep. 1995), vol. 38, No. 19, pp. 3884-3888.

Ko et al., "YC-1, A Novel Activator of Platelet Guanylate Cyclase," Blood, (Dec. 15, 1994), vol. 84, No. 12, pp. 4226-4233.

Kozo et al., "Spontaneous Hypertension in Rats," Int Rev. Exp. Pathol, (1969), vol. 7, pp. 227-270.

Mittendorf et al., "Discovery of Riociguat (BAY 63-2521): A Potent, Oral Stimulator of Soluble Guanylate Cyclase for the Treatment of Pulmonary Hypertension," ChemMedChem, (May 2009), vol. 4, No. 5, pp. 853-865.

Mulsch et al., "Effect of YC-1, An NO-independent, Superoxide-Sensitive Stimulator of Soluble Guanylyl Cyclase, on Smooth Muscle Responsiveness to Nitrovasodilators," British Journal of Pharmacology, (Feb. 1997), vol. 120, No. 4, pp. 681-689.

Olah et al., "Synthesis and Investigation of Organic Fluorine Compounds. XXIII. Preparation of Aromatic Fluorinated Esters as Local Anesthetics," The Journal of Organic Chemistry, (Aug. 1957), vol. 22, No. 8, pp. 879-881.

Palacios et al., "A New and Efficient Synthesis of Imidazo[1,5-a] pyridine Derivatives by a Tandem Aza-Wittig / Electrocyclic Ring Closure of N-vinylic phosphazenes," Tetrahedron, (Mar. 20, 1995), vol. 51, No. 12, pp. 3683-3690.

Pettibone et al., "A Structurally Novel Stimulator of Guanylate Cyclase with Long-Lasting Hypotensive Activity in the Dog," European Journal of Pharmacology, (Oct. 22, 1985), vol. 116, No. 3, pp. 307-312.

Sharkovska et al., "Nitric oxide-independent stimulation of soluble guanylate cyclase reduces organ damage in experimental low-renin and high-renin models," Journal of Hypertension, (Aug. 2010), vol. 28, No. 8, pp. 1666-1675.

Stasch et al., "Soluble Guanylate Cyclase as an Emerging Therapeutic Target in Cardiopulmonary Disease," Circulation, (May 24, 2011), vol. 123, No. 20, pp. 2263-2273.

Van Den Buuse, "Circadian Rhythms of Blood Pressure, Heart Rate, and Locomotor Activity in Spontaneously Hypertensive Rats as Measured With Radio-Telemetry," Physiology & Behavior, (Apr. 1994), vol. 55, No. 4, pp. 783-787.

Wilson et al., "Development of a Scaleable Synthesis of a Partial Nicotinic Acid Receptor Agonist," Organic Process Research & Development, (Mar. 16, 2009), vol. 13, No. 3, pp. 543-547.

Winn et al., "2-(Alkylamino) Nicotinic Acid and Analogs. Potent Angiotensin II Antagonists," Journal of Medicinal Chemistry, (Sep. 1993), vol. 36, No. 18, pp. 2676-2688.

Witte et al., "Experimental heart failure in rats: effects on cardiovascular circadian rhythms and on myocardial $\beta$-adrenergic signaling," Cardiovascular Research, (Aug. 2000), vol. 47, No. 2, pp. 350-358.

Wunder et al., "A cell-based cGMP assay useful for ultra-high-throughput screening and identification of modulators of the nitric oxide/cGMP pathway," Analytical Biochemistry, (Apr. 1, 2005), vol. 339, No. 1, pp. 104-112.

Wu et al., "YC-1 Inhibited Human Platelet Aggregation Through NO-Independent Activation of Soluble Guanylate Cyclase," British Journal of Pharmacology, (Oct. 1995), vol. 116, No. 3, pp. 1973-1978.

Yu et al., "Vasorelaxant Effect of Isoliquiritigenin, a Novel Soluble Guanylate Cyclase Activator, in Rat Aorta," British Journal of Pharmacology, (Apr. 1995), vol. 114, No. 8, pp. 1587-1594.

International Search Report issued on Apr. 10, 2013, by the European Patent Office as the International Searching Authority in corresponding International Application No. PCT/EP2013/050179. (8 pages).

International Preliminary Report on Patentability (Form PCT/IB/373) and the Written Opinion of the International Searching Authority (Form PCT/ISA/237) issued on Jul. 15, 2014, in corresponding International Application No. PCT/EP2013/050179. (13 pages).

\* cited by examiner

SUBSTITUTED TRIAZINE DERIVATIVES AND USE THEREOF AS STIMULATORS OF SOLUBLE GUANYLATE CYCLASE

The present application relates to novel substituted triazines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: The particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory centre. This is of central importance for the activation mechanism. NO can bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, arteriosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attack at the central iron atom of haem. In addition to the side effects, the development of tolerance is one of the crucial disadvantages of this mode of treatment.

In recent years, some substances have been described which stimulate soluble guanylate cyclase directly, i.e. without prior release of NO, such as, for example, 3-(5'-hydroxymethyl-2'-furyl)-1-benzylindazole [YC-1; Wu et al., *Blood* 84 (1994), 4226; Mülsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223).

As stimulators of soluble guanylate cyclase, WO 00/06568 and WO 00/06569 disclose fused pyrazole derivatives, and WO 03/095451 discloses carbamate-substituted 3-pyrimidinylpyrazolopyridines. 3-Pyrimidinylpyrazolopyridines with phenylamide substituents are described in E. M. Becker et al., *BMC Pharmacology* 1 (13), 2001. WO 2004/009590 describes pyrazolopyridines with substituted 4-aminopyrimidines for the treatment of CNS disorders. WO 2010/065275 discloses substituted pyrrolo- and dihydropyridopyrimidines as sGC activators.

It was an object of the present invention to provide novel substances which act as stimulators of soluble guanylate cyclase and which have an identical or improved therapeutic profile compared to the compounds known from the prior art, for example with respect to their in vivo properties such as their pharmacokinetic and pharmacodynamic behaviour and/or their metabolic profile and/or their dose-effect relationship.

The present invention provides compounds of the general formula (I)

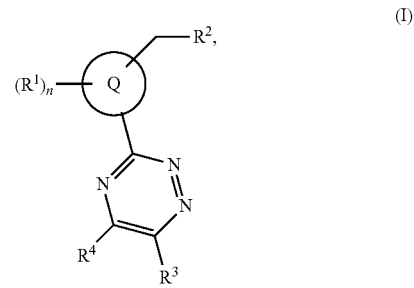

in which the ring Q is 8- or 9-membered heteroaryl, $R^1$ is halogen, cyano, difluoromethyl, trifluoromethyl, $(C_1-C_4)$-alkyl, hydroxyl, oxo or $(C_1-C_4)$-alkoxy, n is a number 0, 1 or 2, $R^2$ is trifluoromethyl, $(C_1-C_6)$-alkyl, $(C_3-C_8)$-cycloalkyl, phenyl or 5- or 6-membered heteroaryl, where $(C_1-C_6)$-alkyl is substituted by a substituent selected from the group consisting of difluoromethyl and trifluoromethyl, where $(C_1-C_6)$-alkyl may be substituted by 1 to 3 fluorine substituents, where $(C_3-C_8)$-cycloalkyl may be substituted by 1 or 2 substituents independently of one another selected from the group consisting of fluorine, methyl and methoxy, where phenyl is substituted by 1 to 3 fluorine substituents, where phenyl may be substituted by 1 or 2 substituents independently of one another selected from the group consisting of methyl and methoxy, and where 5- and 6-membered heteroaryl may be substituted by 1 or 2 substituents independently of one another selected from the group consisting of fluorine and methyl, $R^3$ is difluoromethyl, trifluoromethyl, $(C_1-C_6)$-alkyl, $(C_3-C_7)$-cycloalkyl, $(C_1-C_6)$-alkylsulphonylamino, $(C_1-C_6)$-alkoxycarbonylamino, phenyl or 5- or 6-membered heteroaryl, where $(C_1-C_6)$-alkyl, phenyl and 5- or 6-membered heteroaryl may be substituted by 1 to 3 substituents independently of one another selected from the group consisting of halogen, trifluoromethyl, $(C_1-C_4)$-alkyl, $(C_3-C_7)$-cycloalkyl, difluoromethoxy, trifluoromethoxy and $(C_1-C_6)$-alkoxy, R[4] is hydroxy or amino, and the N-oxides, salts, solvates, salts of the N-oxides and solvates of the N-oxides or salts thereof.

Compounds according to the invention are the compounds of the formula (I) and their salts, solvates and solvates of the salts, the compounds encompassed by formula (I) of the formulae mentioned below and their salts, solvates and solvates of the salts and the compounds encompassed by formula (I) and mentioned below as working examples, and their salts, solvates and solvates of the salts, if the compounds encompassed by formula (I) and mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates is the term used to refer to those forms of the compounds according to the invention which, in the solid or liquid state, form a complex by coordination with solvent molecules. Hydrates are a specific form of solvates in which the coordination is with water. Preferred solvates in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to a person skilled in the art, for example by the methods described below and the procedures described in the working examples, by using corresponding isotopic modifications of the respective reagents and/or starting compounds.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the context of the present invention, the substituents, unless specified otherwise, each have the following meaning:

Alkyl in the context of the invention is a linear or branched alkyl radical having the number of carbon atoms specified in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

5- to 7-membered saturated or partly unsaturated carbocycle in the context of the present invention is a saturated or partly unsaturated cyclic alkyl radical having the number of carbon atoms specified in each case. The following may be mentioned by way of example and by way of preference: cyclopentyl, cyclohexyl, cycloheptyl, cyclopentenyl, cyclohexenyl and cycloheptenyl.

Cycloalkyl or carbocycle in the context of the invention is a monocyclic saturated alkyl radical having the number of carbon atoms specified in each case. The following may be mentioned by way of example and by way of preference: cyclopropyl, cyclobutyl, cyclopentyl, cyclohexyl and cycloheptyl.

Alkoxy in the context of the invention is a straight-chain or branched alkoxy radical having 1 to 6 or 1 to 4 carbon atoms. The following may be mentioned by way of example: methoxy, ethoxy, n-propoxy, isopropoxy, 1-methylpropoxy, n-butoxy, iso-butoxy, tert-butoxy, n-pentoxy, isopentoxy, 1-ethylpropoxy, 1-methylbutoxy, 2-methylbutoxy, 3-methylbutoxy and n-hexoxy. Preference is given to a linear or branched alkoxy radical having 1 to 4 carbon atoms. The following may be mentioned by way of example and by way of preference:

methoxy, ethoxy, n-propoxy, isopropoxy, 1-methylpropoxy, n-butoxy, isobutoxy, tert-butoxy.

Alkoxycarbonylamino in the context of the invention is an amino group having a linear or branched alkoxycarbonyl substituent which has 1 to 4 carbon atoms in the alkyl chain and is attached to the nitrogen atom via the carbonyl group. The following may be mentioned by way of example and by way of preference: methoxycarbonylamino, ethoxycarbonylamino, propoxycarbonylamino, n-butoxycarbonylamino, isobutoxycarbonylamino and tert-butoxycarbonylamino.

Alkylsulphonylamino in the context of the invention is an amino group having a linear or branched alkylsulphonyl substituent which has 1 to 6 carbon atoms and is attached to the nitrogen atom via the sulphonyl group. The following may be mentioned by way of example and by way of preference: methylsulphonylamino, ethylsulphonylamino, n-propylsulphonylamino, isopropylsulphonylamino, n-butylsulphonylamino, tert-butylsulphonylamino, n-pentylsulphonylamino and n-hexylsulphonylamino.

5- to 7-membered saturated or partly unsaturated heterocycle in the context of the invention is a saturated or partly unsaturated heterocycle which has a total of 5 to 7 ring atoms and contains one ring heteroatom from the series N, O, S, SO and/or $SO_2$. The following may be mentioned by way of example: pyrrolidinyl, tetrahydrofuranyl, piperidinyl, tetrahydropyranyl, dihydropyrrolyl, dihydropyridyl.

5- or 6-membered heteroaryl in the context of the invention is a monocyclic aromatic heterocycle (heteroaromatic) which has a total of 5 or 6 ring atoms, contains up to three identical or different ring heteroatoms from the series N, O and/or S and is attached via a ring carbon atom or optionally via a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to: pyridyl, pyrimidinyl, pyridazinyl, pyrazinyl and triazinyl.

8- or 9-membered heteroaryl in the context of the invention is a bicyclic aromatic or partly unsaturated heterocycle which has a total of 8 or 9 ring atoms and contains at least two nitrogen atoms and up to two further, identical or different ring heteroatoms from the series N, O and/or S. The following may be mentioned by way of example: dihydrothienopyrazolyl, thienopyrazolyl, pyrazolopyrazolyl, imidazothiazolyl, tetrahydrocyclopentapyrazolyl, dihydrocyclopentapyrazolyl, tetrahydroindazolyl, dihydroindazolyl, indazolyl, pyrazolopyridinyl, tetrahydropyrazolopyridinyl, pyrazolopyrimidinyl, imidazopyridinyl and imidazopyridazinyl.

Halogen in the context of the invention is fluorine, chlorine, bromine and iodine. Preference is given to bromine and iodine.

An oxo group in the context of the invention is an oxygen atom attached to a carbon atom via a double bond.

In the formula of the group which may represent Q, the end point of the line marked by the symbol * or ** does not represent a carbon atom or a $CH_2$ group, but is part of the bond to the respectively indicated atom to which Q is bonded.

If radicals in the compounds according to the invention are substituted, the radicals may be mono or polysubstituted, unless specified otherwise. In the context of the present invention, it is the case that for all radicals which occur more than once, their meaning is independent of the others. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

Preference is given in the context of the present invention to compounds of the formula (I) in which the ring Q is a group of the formula

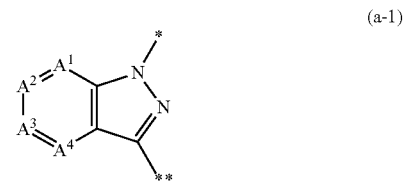

(a-1)

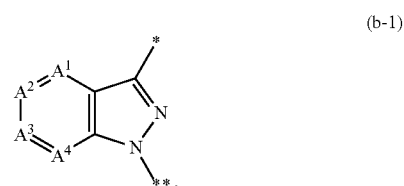

(b-1)

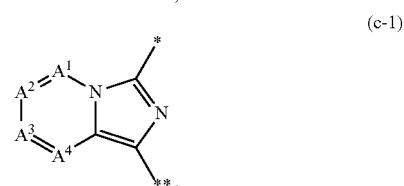

(c-1)

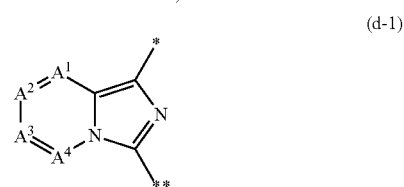

(d-1)

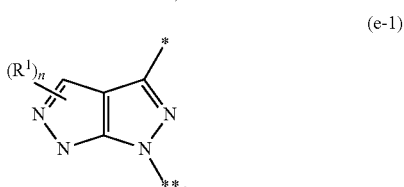

(e-1)

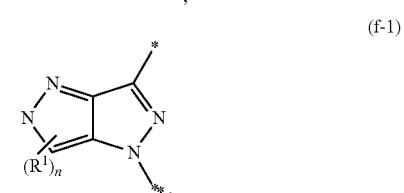

(f-1)

-continued (g-1) 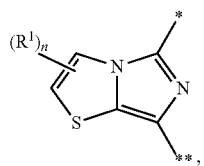

(h-1) 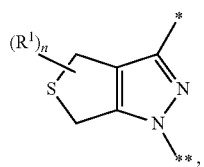

(i-1) 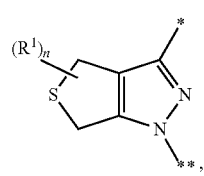

(j-1) 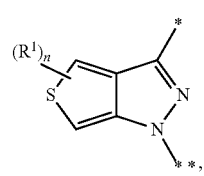

(k-1) 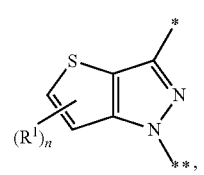

(l-1) 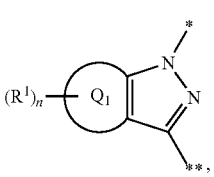

(m-1) 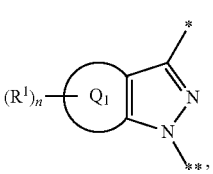

(n-1) 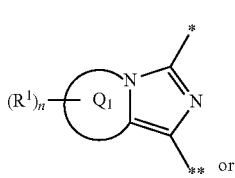

or (o-1) 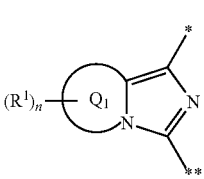

where
* is the attachment site to —$CH_2$—$R^2$,
** is the attachment site to the triazine ring,
the ring $Q_1$ together with the atoms to which it is bonded forms a 5- to 7-membered saturated or partly unsaturated carbocycle or a 5- to 7-membered saturated or partly unsaturated heterocycle,
$R^1$ is fluorine, chlorine or methyl,
n is a number 0, 1 or 2,
$A^1$, $A^2$, $A^3$ and $A^4$ are each independently of one another N, CH or $CR^1$,
with the proviso that not more than two of the $A^1$, $A^2$, $A^3$ and $A^4$ groups are N,
$R^2$ is trifluoromethyl, 2,2,2-trifluoroethyl, 3,3,3-trifluoroprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl,
where phenyl is substituted by 1 to 3 fluorine substituents, and
where cyclopropyl, cyclobutyl, cyclopentyl, cyclohexyl, pyridyl, pyrimidinyl, pyrazinyl and pyridazinyl may be substituted by 1 or 2 fluorine substituents,
$R^3$ is difluoromethyl, trifluoromethyl, ($C_1$-$C_6$)-alkyl, cyclopropyl, cyclobutyl, cyclopentyl, methylsulphonylamino, methoxycarbonylamino, phenyl, pyrazolyl, oxazolyl or pyridyl,
where ($C_1$-$C_6$)-alkyl may be substituted by 1 to 3 substituents independently of one another selected from the group consisting of fluorine, trifluoromethyl, cyclopropyl, cyclobutyl, cyclopentyl, difluoromethoxy, trifluoromethoxy, methoxy and ethoxy,
and
where phenyl, pyrazolyl, oxazolyl and pyridyl may be substituted by 1 or 2 substituents independently of one another selected from the group consisting of fluorine, chlorine, difluoromethyl, trifluoromethyl, methyl, ethyl, cyclopropyl, cyclobutyl, cyclopentyl, trifluoromethoxy, methoxy and ethoxy,
$R^4$ is hydroxy or amino,
and the salts, solvates and solvates of the salts thereof.

In the context of the present invention, preference is also given to compounds of the formula (I) in which the ring Q is a group of the formula (a-1) 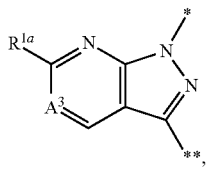

(b-1) 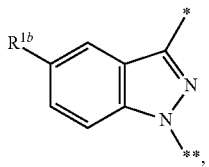

-continued

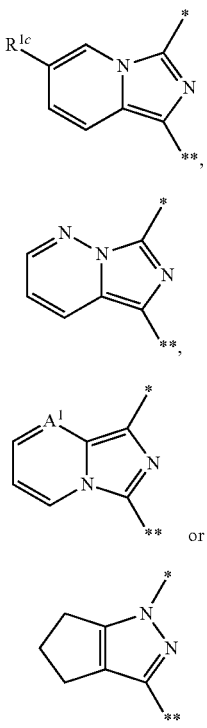

(c-1a)

(c-1a)

(d-1)

(l-1)

where
* is the attachment site to —CH2-R²,
** is the attachment site to the triazine ring,
$R^{1a}$ is hydrogen or methyl,
$R^{1b}$ is hydrogen or fluorine,
$R^{1c}$ is hydrogen or chlorine,
$A^1$ is N or CH,
$A^3$ is N, CH or C—F,
$R^2$ is 3,3,3-trifluoroprop-1-yl, 2,2,3,3-tetrafluoroprop-1-yl, 2,2,3,3,3-pentafluoroprop-1-yl, phenyl or pyridyl,
where phenyl is substituted by 1 to 3 fluorine substituents, and
where pyridyl may be substituted by 1 fluorine substituent,
$R^3$ is difluoromethyl, trifluoromethyl, $(C_1\text{-}C_6)$-alkyl, cyclopropyl, cyclobutyl, cyclopentyl, methylsulphonylamino, methoxycarbonylamino, phenyl, pyrazolyl, oxazolyl or pyridyl,
  where $(C_1\text{-}C_6)$-alkyl may be substituted by 1 to 3 substituents independently of one another selected from the group consisting of fluorine, trifluoromethyl, cyclopropyl, cyclobutyl, cyclopentyl, difluoromethoxy, trifluoromethoxy, methoxy and ethoxy,
  and
  where phenyl, pyrazolyl, oxazolyl and pyridyl may be substituted by 1 or 2 substituents independently of one another selected from the group consisting of fluorine, chlorine, difluoromethyl, trifluoromethyl, methyl, ethyl, cyclopropyl, cyclobutyl, cyclopentyl, trifluoromethoxy, methoxy and ethoxy,
$R^4$ is hydroxy or amino,
and the salts, solvates and solvates of the salts thereof.

In the context of the present invention, preference is also given to compounds of the formula (I) in which
the ring Q is a group of the formula (a-1a)

(a-1b)

where
* is the attachment site to —CH₂—R²,
** is the attachment site to the triazine ring,
$R^{1a}$ is hydrogen or fluorine,
$R^{1b}$ is hydrogen or methyl,
$R^{1b}$ is hydrogen or methyl,
and the salts, solvates and solvates of the salts thereof.

In the context of the present invention, preference is also given to compounds of the formula (I) in which
$R^2$ is 2-fluorophenyl, 2,3-difluorophenyl or 2,3,6-trifluorophenyl,
and the salts, solvates and solvates of the salts thereof.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the compounds of the formula (I) according to the invention, characterized in that

[A] a compound of the formula (II)

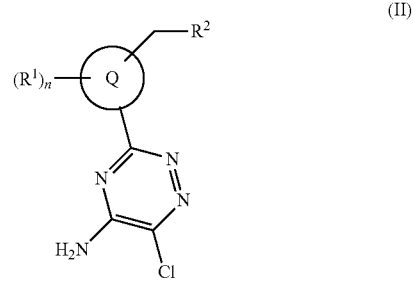

(II)

in which n, Q, $R^1$ and $R^2$ each have the meanings given above
is reacted in an inert solvent in the presence of a suitable transition metal catalyst with a compound of the formula (III)

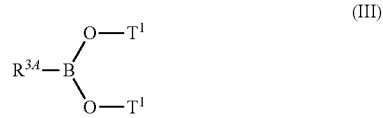

(III)

in which
R³·⁴ is phenyl or 5- or 6-membered heteroaryl,
where phenyl and 5- or 6-membered heteroaryl may be substituted by 1 to 3 substituents independently of one another selected from the group consisting of halogen, trifluoromethyl, $(C_1$-$C_4)$-alkyl, $(C_3$-$C_7)$-cycloalkyl, difluoromethoxy, trifluoromethoxy and $(C_1$-$C_6)$-alkoxy,
and
T¹ is hydrogen or $(C_1$-$C_4)$-alkyl, or both $R^{11}$ radicals together form a —C(CH₃)₂—C(CH₃)₂— bridge,
to give a compound of the formula (I-A)

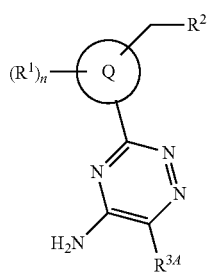

(I-A)

in which n, Q, R¹, R² and R³·⁴ each have the meanings above,
or
[B] a compound of the formula (IV)

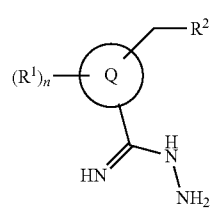

(IV)

in which n, Q, R' and R² each have the meanings above,
is reacted in an inert solvent with a compound of the formula (V)

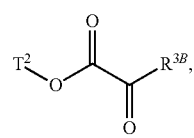

(V)

in which
R³·ᴮ is difluoromethyl, trifluoromethyl, $(C_1$-$C_6)$-alkyl or $(C_3$-$C_7)$-cycloalkyl,
where $(C_1$-$C_6)$-alkyl may be substituted by 1 to 3 substituents independently of one another selected from the group consisting of halogen, trifluoromethyl, $(C_1$-$C_4)$-alkyl, $(C_3$-$C_7)$-cycloalkyl, difluoromethoxy, trifluoromethoxy and $(C_1$-$C_6)$-alkoxy,
and
T² is $(C_1$-$C_4)$-alkyl,
to give a compound of the formula (I-B)

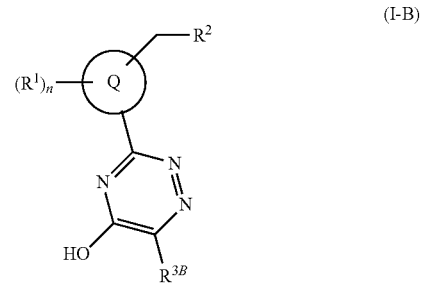

(I-B)

in which n, Q, R¹, R² and R³·ᴮ each have the meanings above,
or
[C] a compound of the formula (I-B) is converted with phosphoryl chloride into a compound of the formula (VI)

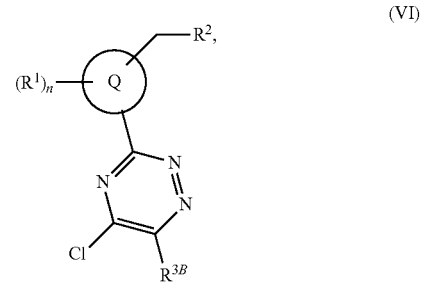

(VI)

in which n, Q, R¹, R² and R³·ᴮ each have the meanings above,
and this is reacted directly with ammonia to give a compound of the formula (I-C)

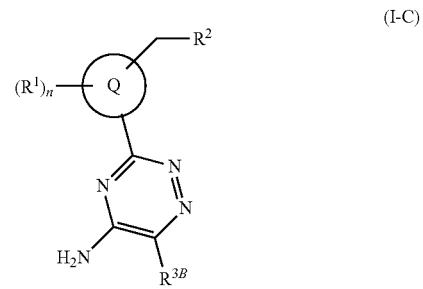

(I-C)

in which n, Q, R¹, R² and R³·ᴮ each have the meanings above,
and the resulting compounds of the formulae (I-A), (I-B) and (I-C) are, where appropriate, converted with the appropriate (i) solvents and/or (ii) acids or bases into their solvates, salts and/or solvates of the salts.

Process step (II)+(III)→(I-A) is carried out in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to acetonitrile.

Optionally, the conversion (II)+(III)→(I-A) can be effected in the presence of a suitable palladium and/or copper catalyst. A suitable palladium catalyst is, for example, palladium on activated carbon, palladium(II) acetate, tetrakis(triphenylphosphine)palladium(0), bis(triphenylphosphine)palladium(II) chloride, bis(acetonitrile)palladium(II) chloride and [1,1'-bis(diphenylphosphino)ferrocene]dichloropalladium(II) and the corresponding dichloromethane complex, optionally in conjunction with additional phosphane ligands, for example (2-biphenyl)di-tert-butylphosphine, dicyclohexyl[2',4',6'-tris(1-methylethyl)biphenyl-2-yl]phosphane (XPHOS), bis(2-phenylphosphinophenyl) ether (DPEphos) or 4,5-bis(diphenylphosphino)-9,9-dimethylxanthene (Xantphos) [cf., for example, Hassan J. et al., *Chem. Rev.* 102, 1359-1469 (2002)]. Suitable copper catalysts are, for example, copper bronze, copper(I) oxide, copper (I) iodide or copper(I) bromide.

The conversion (II)+(III)→(I-A) is effected in the presence of a suitable base. Suitable bases for this conversion are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or cesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using sodium hydride or cesium carbonate.

The reaction (II)+(III)→(I-A) is generally carried out in a temperature range from 0° C. to +200° C., preferably at from +10° C. to +150° C. The conversion can be carried out at atmospheric, elevated or reduced pressure (for example from 0.5 to 5 bar). The reaction is generally carried out at atmospheric pressure.

If the $R^{3A}$ radical is unsaturated, it can subsequently be fully or partly saturated. The reduction is effected with hydrogen in conjunction with transition metal catalysts, for example palladium (10% on activated carbon), Raney nickel or palladium hydroxide. The reduction is generally carried out in a temperature range from +20° C. to +50° C. The reaction can be performed at atmospheric or elevated pressure (for example in the range from 0.5 to 5 bar). The reaction is generally carried out at atmospheric pressure.

Inert solvents for the process step (IV)+(V)→(I-B) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is likewise possible to use mixtures of the solvents mentioned. Preference is given to methanol or ethanol.

The reaction (IV)+(V)→(I-B) is effected generally within a temperature range from +50° C. to +120° C., preferably from +50° C. to +100° C., optionally in a microwave. The conversion can be performed at atmospheric or elevated pressure (for example in the range from 0.5 to 5 bar). The reaction is generally carried out at atmospheric pressure.

The reaction (I-B)→(VI) can be carried out in a solvent which is inert under the reaction conditions, or without solvent. The preferred solvent is sulpholane.

The reaction (I-B)→(VI) is generally carried out in a temperature range from +70° C. to +150° C., preferably from +80° C. to +130° C., optionally in a microwave. The conversion can be performed at atmospheric or elevated pressure (for example in the range from 0.5 to 5 bar). The reaction is generally carried out at atmospheric pressure.

Especially preferably, the conversion (I-B)→(VI) is carried out without solvent in a temperature range from 0° C. to +50° C. at atmospheric pressure.

Process step (VI)→(I-C) is carried out in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to acetonitrile.

The reaction (VI)→(I-C) is effected generally within a temperature range from +20° C. to +100° C., preferably from +40° C. to +70° C., optionally in a microwave. The conversion can be performed at atmospheric or elevated pressure (for example in the range from 0.5 to 5 bar). The reaction is generally carried out at atmospheric pressure.

Preferably, the conversions (I-B)→(VI)→(I-C) are effected without isolation of the intermediate (VI).

The preparation process described can be illustrated by way of example by the following synthesis schemes (Schemes 1, 2 and 3):

Scheme 1

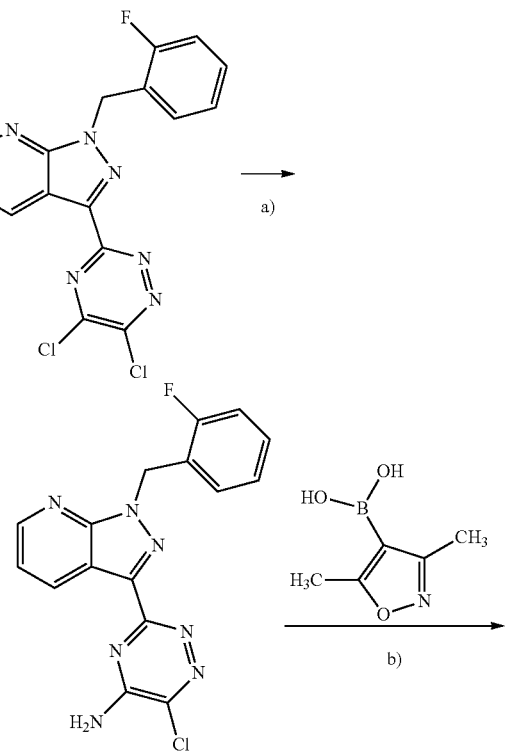

15
-continued
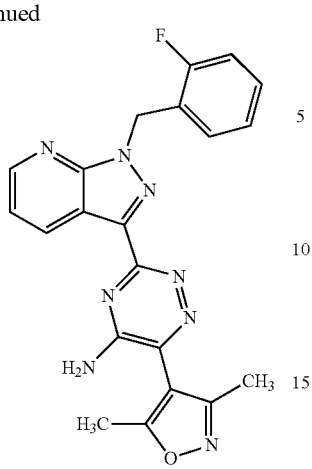
[a]: NH₃ in EtOH, THF, 0° C. → RT; b): PdCl₂(dppf)₂, K₂CO₃, H₂O, dioxane, microwave, 140° C.].
16
-continued
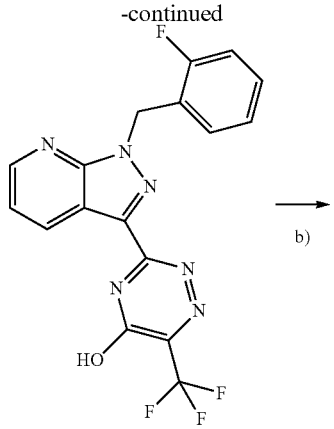
Scheme 2
[a]: EtOH, reflux; b): 1. POCl₃, RT: NH₃ (25% strength), acetonitrile, RT → 50° C].
Scheme 3
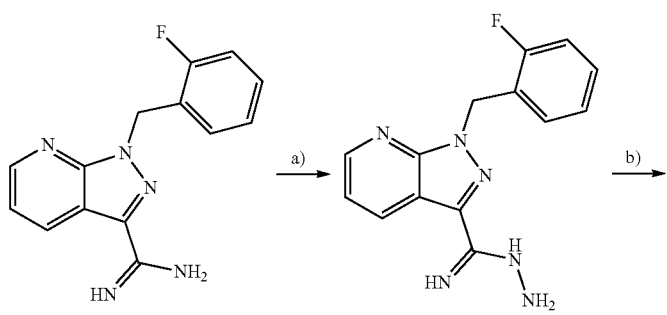

-continued

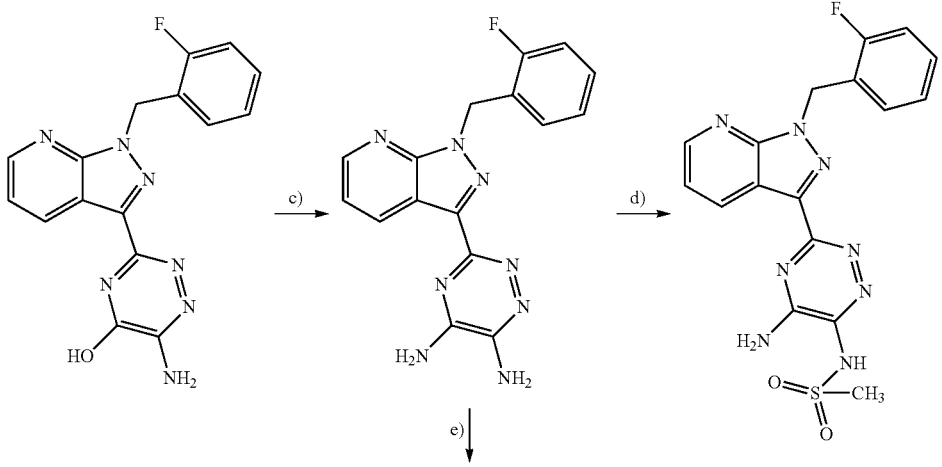

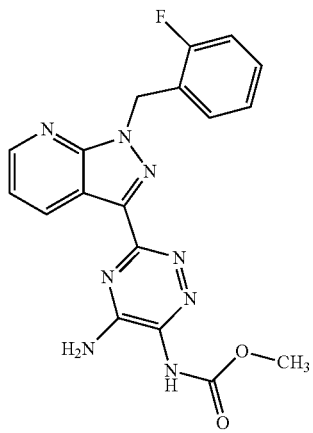

[a): hydrazine hydrate, EtOH, RT; b): ethyl amino (thioxo) acetate, MeOH, NEt₃, reflux: c): (1) SOCl₂, reflux, (2) ammonia solution; ACN, RT; d): methanesulphonyl chloride, NEt₃, RT; e) methyl chloroformate, NEt₃, RT].

The compounds of the formulae (III) and (V) are commercially available, known from the literature or can be prepared in analogy to literature processes.

Further compounds according to the invention can optionally also be prepared by conversions of functional groups of individual substituents, especially those listed for L and $R^3$, proceeding from compounds of the formula (I) obtained by the above processes. These conversions are performed by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester cleavage, etherification, ether cleavage, formation of carbonamides, and introduction and removal of temporary protective groups.

The compounds of the formula (II) can be prepared by reacting a compound of the formula (VI)

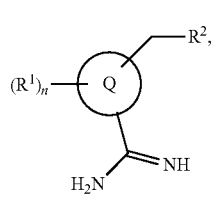

(VI)

in which n, Q, R' and $R^2$ each have the meanings above, in an inert solvent in the presence of a suitable base with hydrazine hydrate to give a compound of the formula (IV)

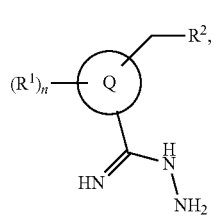

(IV)

in which n, Q, R' and $R^2$ each have the meanings above, this is then converted in an inert solvent with ethyl oxoacetate to a compound of the formula (VII)

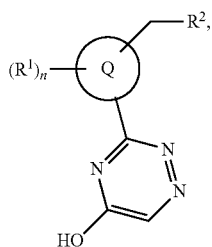
(II-A)

in which n, Q, R¹ and R² each have the meanings above, and this is reacted with thionyl chloride to give a compound of the formula (II).

The synthesis scheme below (Scheme 4) illustrates the process described above:

Scheme 4

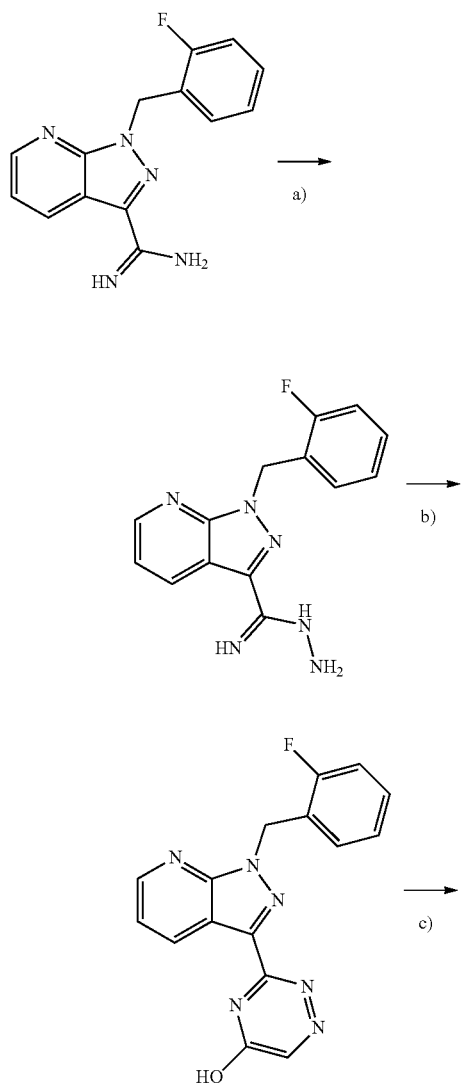

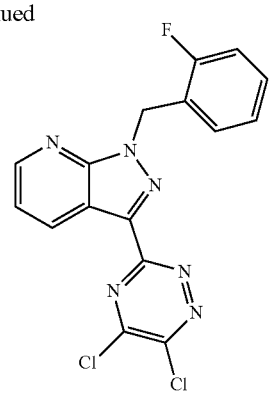

[a): hydrazine hydrate, NEt₃, EtOH, RT: b): ethyl oxoacetate, EtOH reflux; c): thionyl chloride, reflux].

The compounds of the formula (VI) are known from the literature (see, for example WO 2010/065275, WO 2011/115804 and WO 2011/149921) or can be prepared in analogy to processes known from the literature.

The compounds according to the invention are potent stimulators of soluble guanylate cyclase, have valuable pharmacological properties and have an improved therapeutic profile, for example with respect to their in vivo properties and/or their pharmacokinetic characteristics. They are therefore suitable for the treatment and/or prophylaxis of diseases in humans and animals.

The compounds according to the invention bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the compounds according to the invention enhance the action of substances which increase the cGMP level, for example EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term heart failure also includes more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

In addition, the compounds according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity and of combined hyperlipidaemias and metabolic syndrome.

The compounds according to the invention can additionally be used for the treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic overactive bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds according to the invention are furthermore suitable for the treatment and/or prophylaxis of kidney disorders, in particular of acute and chronic renal insufficiency and acute and chronic renal failure. In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions on glomerulae and arterioles, tubular dilatation, hyperphosphataemia and/or need for dialysis. The present invention also encompasses the use of the compounds according to the invention for the treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinisation, multiple sclerosis, thalamic degeneration, Creutzfeld-Jacob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

Furthermore, the compounds according to the invention are also suitable for regulating cerebral blood flow and are thus effective agents for control of migraine. They are also suitable for prophylaxis and control of sequelae of cerebral infarction (cerebral apoplexy) such as stroke, cerebral ischaemia and craniocerebral trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds according to the invention are furthermore suitable for controlling postoperative scarring, for example as a result of glaucoma operations.

The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides for the use of the compounds according to the invention for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds according to the invention for use in a method for treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds according to the invention for production of a medicament for the treatment and/or prophylaxis of disorders, especially of the aforementioned disorders.

The present invention further provides for the use of the compounds according to the invention for producing a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds according to the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

- organic nitrates and NO donors, for example sodium nitroprusside, nitroglycerin, isosorbide mononitrate, isosorbide dinitrate, molsidomine or SIN-1, and inhaled NO;
- compounds which inhibit the breakdown of cyclic guanosine monophosphate (cGMP), for example inhibitors of phosphodiesterases (PDE) 1, 2 and/or 5, in particular PDE 5 inhibitors such as sildenafil, vardenafil and tadalafil;
- agents having antithrombotic activity, for example and with preference from the group of platelet aggregation inhibitors, of anticoagulants or of profibrinolytic substances;
- active compounds lowering blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
- active compounds altering lipid metabolism, for example and with preference from the group of thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, dabigatran, melagatran, bivalirudin or clexane.

In a preferred embodiment of the invention, the compounds according to the invention are administered in combination with a GPIIb/IIIa antagonist such as, by way of example and with preference, tirofiban or abciximab.

In a preferred embodiment of the invention, the compounds according to the invention are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the compounds according to the invention are administered in combination with a CETP inhibitor, by way of example and with preference dalcetrapib, BAY 60-5521, anacetrapib oder CETP vaccine (CETi-1).

In a preferred embodiment of the invention, the inventive compounds are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, a preferred example being orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, non-toxic, pharmaceutically suitable excipients, and for the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Administration forms which function according to the prior art, release the compounds according to the invention rapidly and/or in a modified manner and contain the compounds according to the invention in crystalline and/or amorphized and/or dissolved form are suitable for oral administration, such as e.g. tablets (non-coated or coated tablets, for example with enteric coatings or coatings that dissolve in a delayed manner or are insoluble and control the release of the compound according to the invention), tablets or films/oblates, films/lyophilisates or capsules which disintegrate rapidly in the oral cavity (for example hard or soft gelatine capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilisates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be done in a manner known per se, by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration figures for liquid/liquid solutions are each based on volume.

A. EXAMPLES

Abbreviations and Acronyms
 aq. aqueous solution
 calc. calculated
 DCI direct chemical ionization (in MS)
 DMF dimethylformamide
 DMSO dimethyl sulphoxide
 eq. equivalent(s)
 ESI electrospray ionization (in MS)
 Et ethyl
 h hour(s)
 HPLC high-pressure, high-performance liquid chromatography
 HRMS high-resolution mass spectrometry
 conc. concentrated
 LC/MS liquid chromatography-coupled mass spectrometry
 LiHMDS lithium hexamethyldisilazide
 Me methyl
 min minute(s)
 MS mass spectrometry
 NMR nuclear magnetic resonance spectrometry
 Pd/C palladium on activated carbon (10%)
 Ph phenyl
 RT room temperature
 $R_t$ retention time (in HPLC)
 t-Bu tert-butyl
 TFA trifluoroacetic acid
 THF tetrahydrofuran
 UV ultraviolet spectrometry
 v/v ratio by volume (of a solution)
 XPHOS dicyclohexyl(2',4',6'-triisopropylbiphenyl-2-yl)phosphine LC/MS Methods:

Method 1:

Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2:

Instrument: Waters ACQUITY SQD UPLC System; column: Waters Acquity UPLC HSS T3 1.8µ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.

Method 3:

Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 4:

Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 5:

Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Starting Materials and Intermediates:

Example 1A 1-(2-Fluorobenzyl)-1H-pyrazolo[3,4-b]pyridine-3-carboximidamide hydrochloride

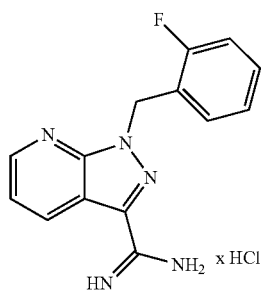 [SMILES: N=C(N)c1nn(Cc2ccccc2F)c2ncccc12]

The synthesis of this compound is described in WO 03/095, 451, example 6A.

Example 2A 1-(2-Fluorobenzyl)-1H-pyrazolo[3,4-b]pyridine-3-carboximidohydrazide

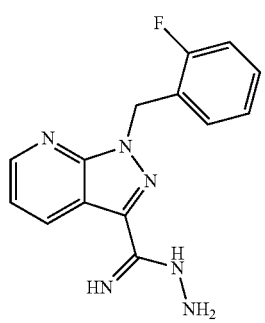 [SMILES: N=C(NN)c1nn(Cc2ccccc2F)c2ncccc12]

50.000 g (163.535 mmol) of 1-(2-fluorobenzyl)-1H-pyrazolo[3,4-b]pyridine-3-carboximidamide hydrochloride were dissolved in 700 ml of ethanol, and 66.192 g (654.141 mmol) of triethylamine and 10.233 g (163.535 mmol) of hydrazine hydrate (80% strength solution in water) were added at 0° C. The mixture was stirred at RT overnight and then concentrated on a rotary evaporator. The residue was taken up in ethyl acetate and the solution was washed three times with saturated aqueous sodium chloride solution. The organic phase was dried over sodium sulphate and concentrated on a rotary evaporator. The residue was stirred with diethyl ether, filtered off with suction and dried under high vacuum. 46.49 g (46% of theory, 68% pure) of the title compound were obtained.

LC-MS (Method 5): $R_t$=0.64 min; MS (ESIpos): m/z=285 $(M+H)^+$

Example 3A

3-[1-(2-Fluorobenzyl)-1H-pyrazolo[3,4-b]pyridin-3-yl]-1,2,4-triazin-5-ol

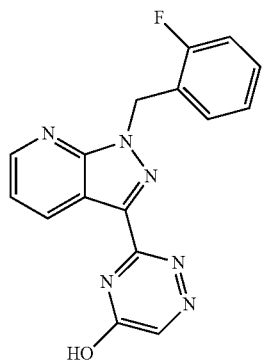 [SMILES: Oc1cnnc(-c2nn(Cc3ccccc3F)c3ncccc23)n1]

22.000 g (purity 68%, approx. 52.621 mmol) of 1-(2-fluorobenzyl)-1H-pyrazolo[3,4-b]pyridine-3-carboximidohydrazide in 220 ml of ethanol were initially introduced, admixed dropwise with 18.265 (89.455 mmol) of ethyl oxoacetate (50% strength solution in toluene) and heated under reflux overnight. The resulting suspension was concentrated on a rotary evaporator and stirred with diethyl ether. The solid was filtered off with suction and dried under high vacuum. Further purification was effected by chromatography on silica gel (mobile phase: dichloromethane/methanol, gradient 30:1→10:1). This gave 12.07 g of the target compound (purity 69%; 49% of theory).

LC-MS (Method 1): $R_t$=0.80 min; MS (ESIpos): m/z=323 $(M+H)^+$

Example 4A 3-(5,6-Dichloro-1,2,4-triazin-3-yl)-1-(2-fluorobenzyl)-1H-pyrazolo[3,4-b]pyridine

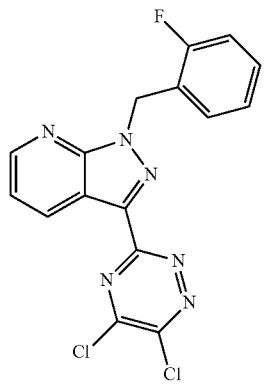 [SMILES: Fc1ccccc1Cn1nc(-c2nnc(Cl)c(Cl)n2)c2cccnc21]

12.000 g (purity 69%, approx. 25.690 mmol) of 3-[1-(2-fluorobenzyl)-1H-pyrazolo[3,4-b]pyridin-3-yl]-1,2,4-triazin-5-ol in 70 ml of thionyl chloride were heated under reflux for 6 h. The reaction mixture was concentrated on a rotary evaporator and admixed with toluene, concentrated again and dried under high vacuum. This gave 13.10 g of the target compound (purity 38%; 52% of theory).

LC-MS (Method 1): R$_t$=1.22 min; MS (ESIpos): m/z=375 (M+H)$^+$

Example 5A

6-Chloro-3-[1-(2-fluorobenzyl)-1H-pyrazolo[3,4-b]pyridin-3-yl]-1,2,4-triazine-5-amine

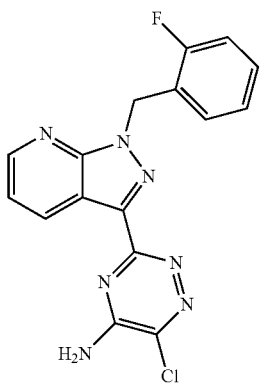 [SMILES: Nc1nc(-c2nn(Cc3ccccc3F)c3ncccc23)nnc1Cl]

7.000 g (purity 38%, 7.090 mmol) of 3-(5,6-dichloro-1,2,4-triazin-3-yl)-1-(2-fluorobenzyl)-1H-pyrazolo[3,4-b]pyridine in 200 ml of absolute THF were initially introduced. With ice-cooling, 4.254 ml (8.508 mmol) of 2N ammonia solution in ethanol were added and the mixture was stirred for 1 h at 0° C. Again with ice-cooling, 4.254 ml (8.508 mmol) of 2N ammonia solution in ethanol were added and the mixture was stirred for 1.5 h at RT. 30 ml (60.000 mmol) of 2N ammonia solution in ethanol was added and the mixture was stirred for 15 min at RT. The reaction mixture was concentrated on a rotary evaporator, suspended in 100 ml of dichloromethane, admixed with 50 ml (100.00 mmol) of 2N ammonia solution in ethanol and stirred for 2 h at RT. The mixture was concentrated on a rotary evaporator and purified by chromatography on silica gel (mobile phase: dichloromethane/methanol, gradient 20:1→10:1). The product-containing fractions were concentrated and stirred with DMSO. The solid was filtered off with suction, after-washed with acetonitrile and dried under high vacuum. The residue was purified by preparative HPLC (mobile phase: acetonitrile/water, gradient 20:80→100:0). This gave 1.68 g of the target compound (purity 65%; 43% of theory).

LC-MS (Method 1): Rt=0.87 min; MS (ESIpos): m/z=356 (M+H)$^+$

Example 6A

6-Amino-3-[1-(2-fluorobenzyl)-1H-pyrazolo[3,4-b]pyridin-3-yl]-1,2,4-triazin-5-ol

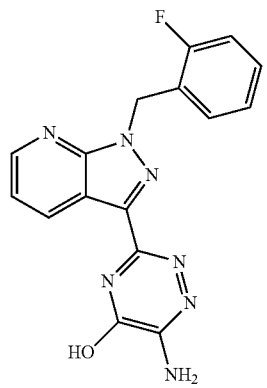 [SMILES: Nc1nnc(-c2nn(Cc3ccccc3F)c3ncccc23)nc1O]

2.000 g (7.035 mmol) of 1-(2-fluorobenzyl)-1H-pyrazolo[3,4-b]pyridine-3-carboximidohydrazide in 50 ml of methanol were initially introduced and admixed with 0.937 g (7.035 mmol) of ethyl amino(thioxo)acetate, and 1.424 g (14.070 mmol) of triethylamine were admixed and the mixture was heated under reflux for 5 h. The reaction mixture was left to stand overnight, and the precipitate was filtered off with suction, washed with a little ethanol and dried under high vacuum. This gave 1.892 g of the target compound (purity 94%; 75% of theory).

LC-MS (Method 1): Rt=0.72 min; MS (ESIpos): m/z=338 (M+H)$^+$

Example 7A

Ethyl 2-fluoro-2-{3-[1-(2-fluorobenzyl)-1H-pyrazolo[3,4-b]pyridin-3-yl]-5-hydroxy-1,2,4-triazin-6-yl}propanoate

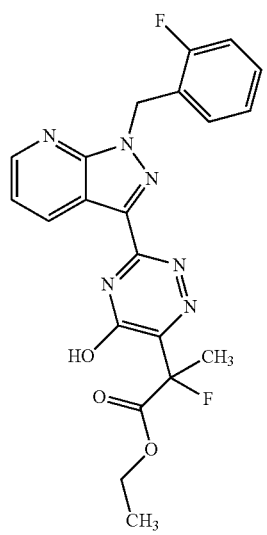 [SMILES: CCOC(=O)C(C)(F)c1nnc(-c2nn(Cc3ccccc3F)c3ncccc23)nc1O]

1.000 g (purity 67%, approx. 2.357 mmol) of 1-(2-fluorobenzyl)-1H-pyrazolo[3,4-b]pyridine-3-carboximidohydrazide in 15 ml of absolute ethanol were initially introduced and admixed with 1.557 g (7.070 mmol) of diethyl 2-fluoro-2-methyl-3-oxobutanedioate (described in *J. Med. Chem.* 1966, 9, 149-151). The mixture was stirred at RT overnight and then concentrated. The residue was purified by preparative HPLC (mobile phase: methanol/water, gradient 30:70→95:5). This gave 230 mg of the target compound (purity 95%; 21% of theory).

LC-MS (Method 2): $R_t$=1.01 min; MS (ESIpos): m/z=441 (M+H)$^+$

Example 8A

2-{5-Amino-3-[1-(2-fluorobenzyl)-1H-pyrazolo[3,4-b]pyridin-3-yl]-1,2,4-triazin-6-yl}-2-fluoropropanamide

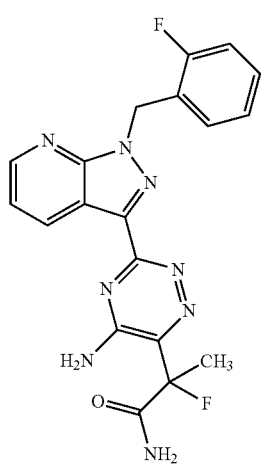 [SMILES: CC(F)(C(N)=O)c1nnc(-c2nn(Cc3ccccc3F)c3ncccc23)nc1N]

250 mg (0.522 mmol) of ethyl 2-fluoro-2-{3-[1-(2-fluorobenzyl)-1H-pyrazolo[3,4-b]pyridin-3-yl]-5-hydroxy-1,2,4-triazin-6-yl}propanoate were admixed with 3 ml of phosphoryl chloride and stirred overnight at RT. The reaction mixture was diluted with 10 ml of dry acetonitrile and, with ice-cooling, stirred into 5 ml of concentrated aqueous ammonia solution (35% strength). Stirring was continued for 2 h at RT and for 16 h at 50° C. After cooling, the precipitate was filtered off with suction and dried in vacuo. This gave 294 mg (purity 95%, quant. yield) of the target compound.

LC-MS (Method 3) Rt=0.96 min; MS (ESIpos): m/z=411 (M+H)$^+$

Working Examples

Example 1

3-[1-(2-Fluorobenzyl)-1H-pyrazolo[3,4-b]pyridin-3-yl]-6-(5-fluoropyridin-3-yl)-1,2,4-triazine-5-amine

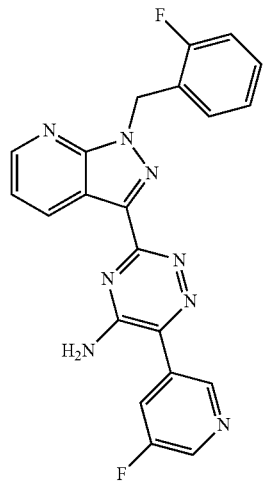 [SMILES: Nc1nc(-c2nn(Cc3ccccc3F)c3ncccc23)nnc1-c1cncc(F)c1]

Under an argon atmosphere, 100 mg (purity 65%, 0.183 mmol) of 6-chloro-3-[1-(2-fluorobenzyl)-1H-pyrazolo[3,4-b]pyridin-3-yl]-1,2,4-triazine-5-amine were suspended in 4 ml of absolute dioxane. 103 mg (0.731 mmol) of (5-fluoropyridin-3-yl)boronic acid and 25 mg (0.183 mmol) of potassium carbonate were added and argon was passed through the suspension for 10 min with stirring. Then, 3 mg (4.020 mol) of 1,1'-bis(diphenylphosphino)ferrocenepalladium(II) chloride were added and again argon was passed through the mixture for 1 min. The reaction mixture was stirred for 20 min in the microwave at 140° C. 5 mg (0.018 mmol) of tricyclohexylphosphine were added and the mixture was again stirred for 20 min in the microwave at 140° C. After cooling, the mixture was filtered over an Extrelut cartridge and afterwashed with a mixture of dichloromethane/methanol (v/v=20:1). The filtrate was concentrated and the residue was purified by preparative HPLC (mobile phase: acetonitrile/water, gradient 20:80→100:0). 59 mg of the target compound were obtained (58% of theory).

LC-MS (Method 4): $R_t$=4.78 min; MS (ESIpos): m/z=417 (M+H)$^+$ $^1$H NMR (400 MHz; DMSO-d$_6$): δ [ppm]=5.92 (s, 2H), 7.17 (t, 1H), 7.23-7.27 (m, 3H), 7.35-7.41 (m, 1H), 7.51 (dd, 1H), 8.08 (dt, 1H), 8.73-8.78 (m, 3H), 8.96 (dd, 1H).

Example 2

3-[1-(2-Fluorobenzyl)-1H-pyrazolo[3,4-b]pyridin-3-yl]-6-(2-methylpyridin-3-yl)-1,2,4-triazine-5-amine

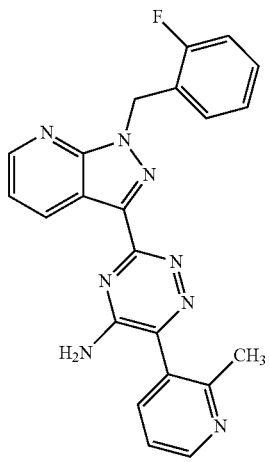 [SMILES: Cc1ncccc1-c1nnc(-c2nn(Cc3ccccc3F)c3ncccc23)nc1N]

Under an argon atmosphere, 140 mg (purity 65%, 0.256 mmol) of 6-chloro-3-[1-(2-fluorobenzyl)-1H-pyrazolo[3,4-b]pyridin-3-yl]-1,2,4-triazine-5-amine were suspended in 5 ml of absolute dioxane. 105 mg (0.767 mmol) of (2-methylpyridin-3-yl)boronic acid, 1.023 ml (1.023 mmol) of 1N aqueous potassium carbonate solution, and 14 mg (0.051 mmol) of tricyclohexylphosphine were added and argon was passed through the suspension with stirring. Then, 28 mg (0.038 mmol) of 1,1'-bis(diphenylphosphino)ferrocenepalladium(II) chloride were added and the reaction mixture was stirred for 30 min in the microwave at 140° C. Again, 19 mg (0.026 mmol) of 1,1'-bis(diphenylphosphino)ferrocenepalladium(II) chloride were added and the reaction mixture was stirred for 40 min in the microwave at 150° C. After cooling, the mixture was filtered over an Extrelut cartridge and after-washed with a mixture of dichloromethane/methanol (v/v=20:1). The filtrate was concentrated and the residue was purified by preparative HPLC (mobile phase: acetonitrile/water, gradient 20:80→100:0). 26 mg of the target compound were obtained (18% of theory).

LC-MS (Method 4): R$_t$=4.27 min; MS (ESIpos): m/z=413 (M+H)$^+$ $^1$H NMR (400 MHz; DMSO-d$_6$): δ [ppm]=2.48 (s, 3H), 5.91 (s, 2H), 7.17 (t, 1H), 7.22-7.27 (m, 2H), 7.35-7.41 (m, 1H), 7.49 (dd, 1H), 7.68 (t, 1H), 8.14 (d, 1H), 8.73 (dd, 1H), 8.77 (d, 1H), 8.95 (dd, 1H).

Example 3

6-(3,5-Dimethyl-1,2-oxazol-4-yl)-3-[1-(2-fluorobenzyl)-1H-pyrazolo[3,4-b]pyridin-3-yl]-1,2,4-triazine-5-amine

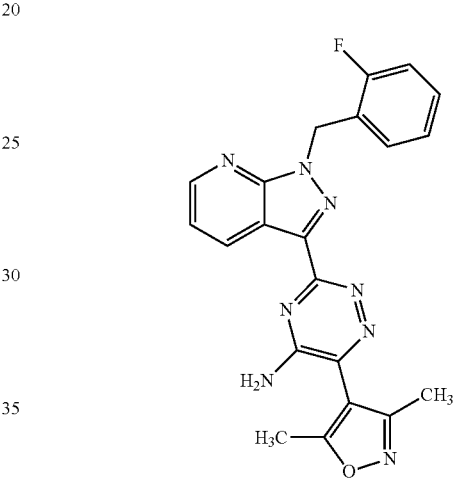

Under an argon atmosphere, 140 mg (purity 65%, 0.256 mmol) of 6-chloro-3-[1-(2-fluorobenzyl)-1H-pyrazolo[3,4-b]pyridin-3-yl]-1,2,4-triazine-5-amine were suspended in 5 ml of absolute dioxane. 154 mg (purity 70%, 0.767 mmol) of (3,5-dimethyl-1,2-oxazol-4-yl)boronic acid, 1.023 ml (1.023 mmol) of 1N aqueous potassium carbonate solution and 14 mg (0.051 mmol) of tricyclohexylphosphine were added and argon was passed through the suspension for 10 min with stirring. Then, 28 mg (0.038 mmol) of 1,1'-bis(diphenylphosphino)ferrocenepalladium(II) chloride were added and the reaction mixture was stirred for 30 min in the microwave at 140° C. The reaction mixture was again stirred for 60 min in the microwave at 140° C. After cooling, the mixture was filtered over an Extrelut cartridge and after-washed with a mixture of dichloromethane/methanol (v/v=20:1). The filtrate was concentrated and the residue was purified by preparative HPLC (mobile phase: acetonitrile/water, gradient 20:80→100:0). This gave 25 mg of the target compound (purity 95%; 18% of theory).

LC-MS (Method 4): R$_t$=4.73 min; MS (ESIpos): m/z=417 (M+H)$^+$ $^1$H NMR (400 MHz; DMSO-d$_6$): δ [ppm]=2.22 (s, 3H), 2.40 (s, 3H), 5.90 (s, 2H), 7.16 (t, 1H), 7.21-7.27 (m, 2H), 7.35-7.41 (m, 1H), 7.48 (dd, 1H), 8.72 (dd, 1H), 8.94 (dd, 1H).

Example 4

3-[1-(2-Fluorobenzyl)-1H-pyrazolo[3,4-b]pyridin-3-yl]-6-(6-methoxypyridin-3-yl)-1,2,4-triazine-5-amine

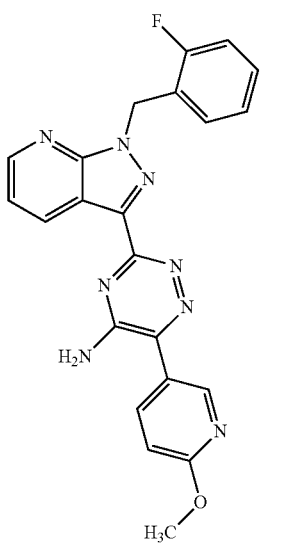 [SMILES: COc1ccc(-c2nnc(-c3nn(Cc4ccccc4F)c4ncccc34)nc2N)cn1]

Under an argon atmosphere, 140 mg (purity 65%, 0.256 mmol) of 6-chloro-3-[1-(2-fluorobenzyl)-1H-pyrazolo[3,4-b]pyridin-3-yl]-1,2,4-triazine-5-amine were suspended in 5 ml of absolute dioxane. 117 mg (0.767 mmol) of (6-methoxypyridin-3-yl)boronic acid, 1.023 ml (1.023 mmol) of 1N aqueous potassium carbonate solution and 14 mg (0.051 mmol) of tricyclohexylphosphine were added and argon was passed through the suspension for 10 min with stirring. Then, 28 mg (0.038 mmol) of 1,1'-bis(diphenylphosphino)ferrocenepalladium(II) chloride were added and the reaction mixture was stirred for 30 min in the microwave at 140° C. After cooling, the mixture was filtered over an Extrelut cartridge and after-washed with a mixture of dichloromethane/methanol (v/v=20:1). The filtrate was concentrated and the residue was purified by preparative HPLC (mobile phase: acetonitrile/water, gradient 20:80→100:0). This gave 58 mg of the target compound (purity 85%; 36% of theory).

LC-MS (Method 4): R$_t$=4.77 min; MS (ESIpos): m/z=429 (M+H)$^+$ $^1$H NMR (400 MHz; DMSO-d$_6$): δ [ppm]=3.96 (s, 3H), 5.92 (s, 2H), 7.02 (d, 1H), 7.16 (t, 1H), 7.21-7.27 (m, 2H), 7.36-7.40 (m, 1H), 7.51 (dd, 1H), 8.03 (dd, 1H), 8.53 (d, 1H), 8.74 (dd, 1H), 8.95 (dd, 1H).

Example 5

3-[1-(2-Fluorobenzyl)-1H-pyrazolo[3,4-b]pyridin-3-yl]-6-(pyridin-4-yl)-1,2,4-triazine-5-amine

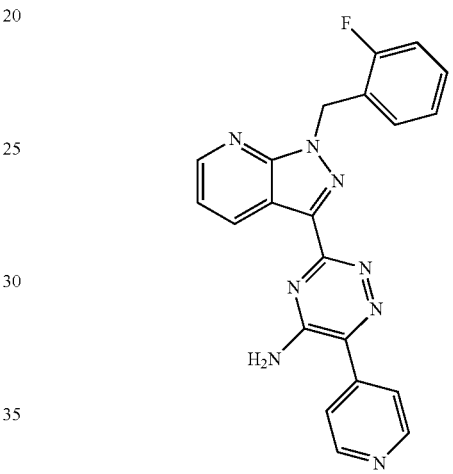

Under an argon atmosphere, 140 mg (purity 65%, 0.256 mmol) of 6-chloro-3-[1-(2-fluorobenzyl)-1H-pyrazolo[3,4-b]pyridin-3-yl]-1,2,4-triazine-5-amine were suspended in 5 ml of absolute dioxane. 122 mg (0.767 mmol) of pyridin-4-ylboronic acid hydrochloride, 1.023 ml (1.023 mmol) of 1N aqueous potassium carbonate solution and 14 mg (0.051 mmol) of tricyclohexylphosphine were added and argon was passed through the suspension for 10 min with stirring. Then, 28 mg (0.038 mmol) of 1,1'-bis(diphenylphosphino)ferrocenepalladium(II) chloride were added and the reaction mixture was stirred for 30 min in the microwave at 140° C. The reaction mixture was again stirred for 60 min in the microwave at 140° C. After cooling, the mixture was filtered over an Extrelut cartridge and after-washed with a mixture of dichloromethane/methanol (v/v=20:1). The filtrate was concentrated and the residue was purified by preparative HPLC (mobile phase: acetonitrile/water, gradient 20:80→100:0). 36 mg of the target compound were obtained (33% of theory).

LC-MS (Method 4): R$_t$=4.41 min; MS (ESIpos): m/z=399 (M+H)$^+$

¹H NMR (400 MHz; DMSO-d₆): δ [ppm]=5.90 (s, 2H), 7.16 (t, 1H), 7.22-7.27 (m, 2H), 7.35-7.41 (m, 1H), 7.48 (dd, 1H), 7.87 (d, 2H), 8.72 (dd, 1H), 8.84 (d, 2H), 8.96 (dd, 1H).

Example 6

3-[1-(2-Fluorobenzyl)-1H-pyrazolo[3,4-b]pyridin-3-yl]-6-(1-methyl-1H-pyrazol-4-yl)-1,2,4-triazine-5-amine

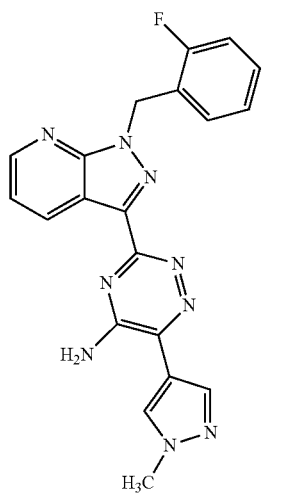 [SMILES: Cn1cc(-c2nnc(-c3nn(Cc4ccccc4F)c4ncccc34)nc2N)cn1]

Under an argon atmosphere, 140 mg (purity 65%, 0.256 mmol) of 6-chloro-3-[1-(2-fluorobenzyl)-1H-pyrazolo[3,4-b]pyridin-3-yl]-1,2,4-triazine-5-amine were suspended in 5 ml of absolute dioxane. 160 mg (0.767 mmol) of 1-methyl-4-(4,4,5,5-tetramethyl-1,3,2-dioxaborolan-2-yl)-1H-pyrazole, 1.023 ml (1.023 mmol) of 1N aqueous potassium carbonate solution and 14 mg (0.051 mmol) of tricyclohexylphosphine were added and argon was passed through the suspension for 10 min with stirring. Then, 28 mg (0.038 mmol) of 1,1'-bis(diphenylphosphino)ferrocenepalladium(II) chloride were added and the reaction mixture was stirred for 30 min in the microwave at 140° C. The reaction mixture was again stirred for 15 min in the microwave at 140° C. After cooling, the mixture was filtered over an Extrelut cartridge and after-washed with a mixture of dichloromethane/methanol (v/v=20:1). The filtrate was concentrated and the residue was purified by preparative HPLC (mobile phase: acetonitrile/water, gradient 20:80→100:0). 66 mg of the target compound were obtained (47% of theory).

LC-MS (Method 4): R_t=4.40 min; MS (ESIpos): m/z=402 (M+H)⁺

¹H NMR (400 MHz; DMSO-d₆): δ [ppm]=3.95 (s, 3H), 5.90 (s, 2H), 7.16 (dt, 1H), 7.22-7.27 (m, 2H), 7.35-7.41 (m, 1H), 7.49 (dd, 1H), 8.04 (s, 1H), 8.41 (s, 1H), 8.73 (dd, 1H), 8.96 (dd, 1H).

Example 7

3-[1-(2-Fluorobenzyl)-1H-pyrazolo[3,4-b]pyridin-3-yl]-6-(pyridin-3-yl)-1,2,4-triazine-5-amine

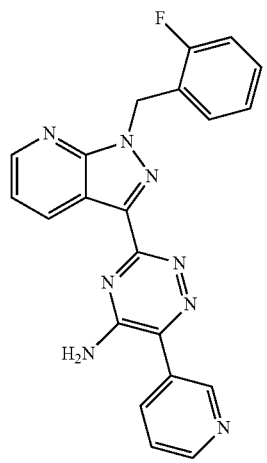 [SMILES: Nc1nc(-c2nn(Cc3ccccc3F)c3ncccc23)nnc1-c1cccnc1]

Under an argon atmosphere, 140 mg (purity 65%, 0.256 mmol) of 6-chloro-3-[1-(2-fluorobenzyl)-1H-pyrazolo[3,4-b]pyridin-3-yl]-1,2,4-triazine-5-amine were suspended in 5 ml of absolute dioxane. 94 mg (0.767 mmol) of pyridin-3-ylboronic acid, 1.023 ml (1.023 mmol) of 1N aqueous potassium carbonate solution and 14 mg (0.051 mmol) of tricyclohexylphosphine were added and argon was passed through the suspension for 10 min with stirring. Then, 28 mg (0.038 mmol) of 1,1'-bis(diphenylphosphino)ferrocenepalladium(II) chloride were added and the reaction mixture was stirred for 30 min in the microwave at 140° C. After cooling, the mixture was filtered over an Extrelut cartridge and after-washed with a mixture of dichloromethane/methanol (v/v=20:1). The filtrate was concentrated and the residue was purified by preparative HPLC (mobile phase: acetonitrile/water, gradient 20:80→100:0). 77 mg of the target compound were obtained (65% of theory).

LC-MS (Method 4): R_t=4.47 min; MS (ESIpos): m/z=399 (M+H)⁺

$^1$H NMR (400 MHz; DMSO-d$_6$): δ [ppm]=5.92 (s, 2H), 7.17 (t, 1H), 7.22-7.27 (m, 2H), 7.36-7.41 (m, 1H), 7.51 (dd, 1H), 7.73 (dd, 1H), 8.27 (dt, 1H), 8.74 (dd, 1H), 8.82 (dd, 1H), 8.96 (dd, 2H).

Example 8

3-[1-(2-Fluorobenzyl)-1H-pyrazolo[3,4-b]pyridin-3-yl]-6-(2-methoxypyridin-3-yl)-1,2,4-triazine-5-amine

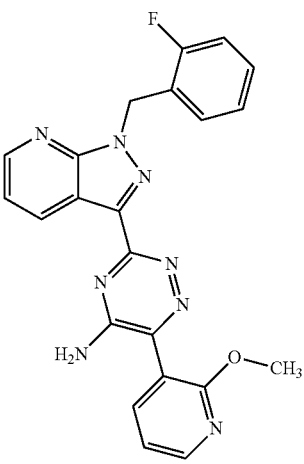 [SMILES: COc1ncccc1-c1nnc(-c2nn(Cc3ccccc3F)c3ncccc23)nc1N]

Under an argon atmosphere, 140 mg (purity 65%, 0.256 mmol) of 6-chloro-3-[1-(2-fluorobenzyl)-1H-pyrazolo[3,4-b]pyridin-3-yl]-1,2,4-triazine-5-amine were suspended in 5 ml of absolute dioxane. 117 mg (0.767 mmol) of (2-methoxypyridin-3-yl)boronic acid, 1.023 ml (1.023 mmol) of 1N aqueous potassium carbonate solution and 14 mg (0.051 mmol) of tricyclohexylphosphine were added and argon was passed through the suspension for 10 min with stirring. Then, 28 mg (0.038 mmol) of 1,1'-bis(diphenylphosphino)ferrocenepalladium(II) chloride were added and the reaction mixture was stirred for 60 min in the microwave at 140° C. After cooling, the mixture was filtered over an Extrelut cartridge and after-washed with a mixture of dichloromethane/methanol (v/v=20:1). The filtrate was concentrated and the residue was purified by preparative HPLC (mobile phase: acetonitrile/water, gradient 20:80→100:0). 38 mg of the target compound were obtained (27% of theory).

LC-MS (Method 4): R$_t$=4.72 min; MS (ESIpos): m/z=429 (M+H)$^+$ $^1$H NMR (400 MHz; DMSO-d$_6$): δ [ppm]=3.32 (s, 2H), 3.90 (s, 3H), 5.88 (s, 2H), 7.13-7.27 (m, 3H), 7.34-7.40 (m, 1H), 7.44 (dd, 1H), 7.53-7.65 (m, 1H), 7.87 (dd, 1H), 8.36 (dd, 1H), 8.69 (dd, 1H), 8.95 (dd, 1H).

Example 9

3-[1-(2-Fluorobenzyl)-1H-pyrazolo[3,4-b]pyridin-3-yl]-6-(2-methylpyridin-4-yl)-1,2,4-triazine-5-amine

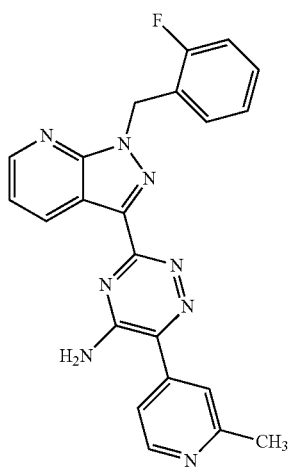 [SMILES: Cc1cc(-c2nnc(-c3nn(Cc4ccccc4F)c4ncccc34)nc2N)ccn1]

Under an argon atmosphere, 140 mg (purity 65%, 0.256 mmol) of 6-chloro-3-[1-(2-fluorobenzyl)-1H-pyrazolo[3,4-b]pyridin-3-yl]-1,2,4-triazine-5-amine were suspended in 5 ml of absolute dioxane. 105 mg (0.767 mmol) of (2-methylpyridin-4-yl)boronic acid, 1.023 ml (1.023 mmol) of 1N aqueous potassium carbonate solution and 14 mg (0.051 mmol) of tricyclohexylphosphine were added and argon was passed through the suspension for 10 min with stirring. Then, 28 mg (0.038 mmol) of 1,1'-bis(diphenylphosphino)ferrocenepalladium(II) chloride were added and the reaction mixture was stirred for 30 min in the microwave at 140° C. Again, 19 mg (0.026 mmol) of 1,1'-bis(diphenylphosphino)ferrocenepalladium(II) chloride were added and the reaction mixture was stirred for 40 min in the microwave at 150° C. After cooling, the mixture was filtered over an Extrelut cartridge and after-washed with a mixture of dichloromethane/methanol (v/v=20:1). The filtrate was concentrated and the residue was purified by preparative HPLC (mobile phase: acetonitrile/water, gradient 20:80→100:0). This gave 53 mg of the target compound (purity 92%; 41% of theory).

LC-MS (Method 4): R$_t$=4.25 min; MS (ESIpos): m/z=413 (M+H)$^+$

¹H NMR (400 MHz; DMSO-$d_6$): δ [ppm]=2.72 (s, 3H), 5.91 (s, 2H), 7.16 (t, 1H), 7.22-7.29 (m, 2H), 7.35-7.41 (m, 1H), 7.49 (dd, 1H), 7.93 (d, 1H), 8.01 (s, 1H), 8.72 (dd, 1H), 8.83 (d, 1H), 8.96 (dd, 1H).

Example 10

3-[1-(2-Fluorobenzyl)-1H-pyrazolo[3,4-b]pyridin-3-yl]-1,2,4-triazine-5,6-diamine

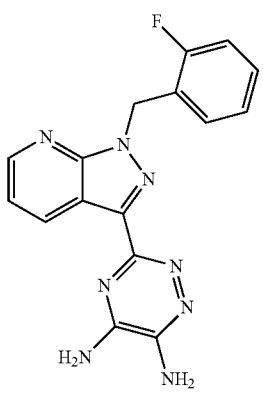 [SMILES: Nc1nnc(-c2nn(Cc3ccccc3F)c3ncccc23)nc1N]

3.602 g (10.677 mmol) of 6-amino-3-[1-(2-fluorobenzyl)-1H-pyrazolo[3,4-b]pyridin-3-yl]-1,2,4-triazin-5-ol in 45 ml of thionyl chloride were added and heated under reflux for 3 h. The reaction mixture was diluted with 200 ml of dry acetonitrile and, with ice-cooling, added dropwise to 500 ml of concentrated aqueous ammonia solution (35% strength). The mixture was stirred at RT overnight. The acetonitrile was removed on a rotary evaporator and the precipitate was filtered off with suction. This gave 3.541 g (purity 67%, 66% of theory) of the target compound. A small amount was purified by preparative HPLC (mobile phase: acetonitrile/water with 0.1% TFA, gradient 30:70→95:5).

LC-MS (Method 1): $R_t$=0.71 min; MS (ESIpos): m/z=337 (M+H)⁺

¹H NMR (400 MHz; DMSO-$d_6$): δ [ppm]=5.90 (s, 2H), 7.13-7.18 (m, 1H), 7.21-7.27 (m, 2H), 7.35-7.41 (m, 1H), 7.45-7.53 (m, 3H), 8.53 (s br, 1H), 8.75 (dd, 1H), 8.84 (dd, 1H), 9.52 (s br, 1H).

Example 11

N-{5-Amino-3-[1-(2-fluorobenzyl)-1H-pyrazolo[3,4-b]pyridin-3-yl]-1,2,4-triazin-6-yl}methanesulphonamide

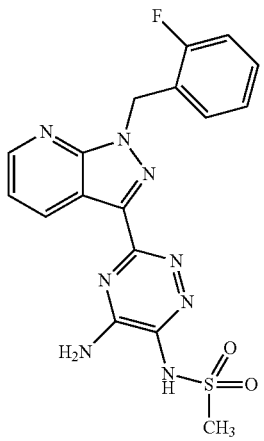 [SMILES: CS(=O)(=O)Nc1nnc(-c2nn(Cc3ccccc3F)c3ncccc23)nc1N]

200 mg (0.595 mmol) of 3-[1-(2-fluorobenzyl)-1H-pyrazolo[3,4-b]pyridin-3-yl]-1,2,4-triazine-5,6-diamine were admixed with 8 ml of dichloromethane and cooled to 0° C. 545 mg (4.757 mmol) of methanesulphonyl chloride and 481 mg (4.757 mmol) of triethylamine were added and the mixture was stirred at RT for 72 h. The mixture was diluted with dichloromethane and the precipitate was filtered off with suction. The filtrate was partitioned between water and ethyl acetate. The organic phase was dried over sodium sulphate and concentrated on a rotary evaporator. The residue was purified by preparative HPLC (mobile phase: acetonitrile/water with 0.1% TFA, gradient 30:70→95:5). This gave 57 mg (18% of theory) of the target compound.

LC-MS (Method 2): Rt=0.77 min; MS (ESIpos): m/z=415 (M+H)⁺

¹H-NMR (400 MHz, TFA-d₁): δ [ppm]=3.47 (s, 3H), 6.05 (s, 2H), 7.08-7.14 (m, 1H), 7.29 (t, 1H), 7.44-7.50 (m, 1H), 7.54-7.60 (m, 1H), 8.09 (dd, 1H), 9.05-9.09 (m, 1H), 9.54 (dd, 1H).

¹H NMR (400 MHz; DMSO-d₆): δ [ppm]=4.00 (s, 3H), 5.79 (s, 2H), 7.11-7.16 (m, 2H), 7.20-7.25 (m, 1H), 7.32-7.40 (m, 2H), 8.00 (d br, 1H), 8.56 (d br, 1H), 8.64 (dd, 1H), 8.75 (dd, 1H), 9.86 (s, 1H).

Example 12

Methyl {5-amino-3-[1-(2-fluorobenzyl)-1H-pyrazolo[3,4-b]pyridin-3-yl]-1,2,4-triazin-6-yl}carbamate

Example 13

3-[1-(2-Fluorobenzyl)-1H-pyrazolo[3,4-b]pyridin-3-yl]-6-(trifluoromethyl)-1,2,4-triazin-5-ol

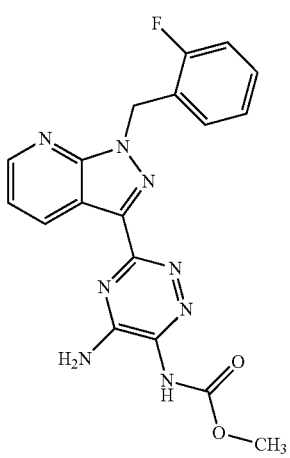 [SMILES: COC(=O)Nc1nnc(-c2nn(Cc3ccccc3F)c3ncccc23)nc1N]

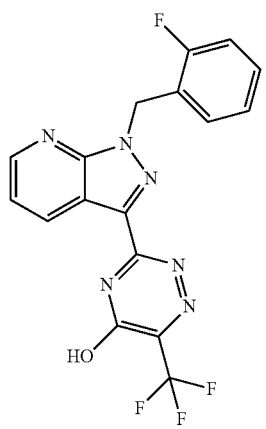 [SMILES: Oc1nc(-c2nn(Cc3ccccc3F)c3ncccc23)nnc1C(F)(F)F]

200 mg (purity 67%, 0.398 mmol) of 3-[1-(2-fluorobenzyl)-1H-pyrazolo[3,4-b]pyridin-3-yl]-1,2,4-triazine-5,6-diamine were admixed with 4 ml of dichloromethane and cooled to 0° C. 151 mg (1.594 mmol) of methyl chloroformate dissolved in 1 ml of dichloromethane and 161 mg (1.594 mmol) of triethylamine were added and the mixture was stirred at RT for 15 min. The precipitate was filtered off with suction and dried under high vacuum. This gave 97 mg (61% of theory) of the target compound.

LC-MS (Method 5): Rt=2.09 min; MS (ESIpos): m/z=395 (M+H)⁺

1.098 g (7.035 mmol) of methyl 3,3,3-trifluoro-2-oxopropanoate in 10 ml of ethanol were initially introduced and heated to reflux. Then, 2.000 g (7.035 mmol) of 1-(2-fluorobenzyl)-1H-pyrazolo[3,4-d]pyrimidine-3-carboximidohydrazide suspended in 25 ml of ethanol were added and the mixture was heated under reflux overnight. After cooling, the mixture was filtered, and the filtercake was washed with a little ethanol and purified by preparative HPLC (mobile phase: acetonitrile/water with 0.1% TFA, ratio 45:55). This gave 710 mg of the target compound (purity 93%; 24% of theory).

LC-MS (Method 1) Rt=0.97 min; MS (ESIpos): m/z=391 (M+H)⁺

¹H NMR (400 MHz, DMSO-d₆): δ [ppm]=5.94 (s, 2H), 7.12-7.19 (m, 1H), 7.21-7.29 (m, 2H), 7.33-7.42 (m, 1H), 7.55 (dd, 1H), 8.73 (dd, 1H), 8.78 (dd, 1H).

Example 14

3-[1-(2-Fluorobenzyl)-1H-pyrazolo[3,4-b]pyridin-3-yl]-6-(trifluoromethyl)-1,2,4-triazine-5-amine

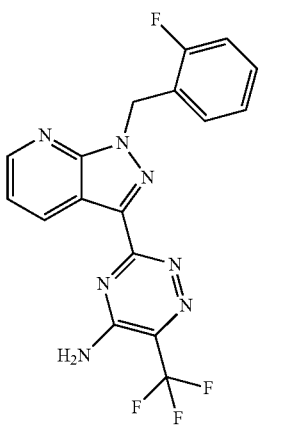 [SMILES: Nc1nc(-c2nn(Cc3ccccc3F)c3ncccc23)nnc1C(F)(F)F]

690 mg (1.768 mmol) of 3-[1-(2-fluorobenzyl)-1H-pyrazolo[3,4-b]pyridin-3-yl]-6-(trifluoromethyl)-1,2,4-triazin-5-ol were admixed with 9 ml of phosphoryl chloride and stirred at RT overnight. The reaction mixture was diluted with 50 ml of dry acetonitrile and, with ice-cooling, stirred into 123 ml of concentrated aqueous ammonia solution (25% strength). Stirring was carried out for 48 h at RT and for 24 h at 50° C. After cooling, the acetonitrile was removed on a rotary evaporator, water was added, the precipitate was filtered off with suction and the filtercake was washed with a little water. The residue was purified by preparative HPLC (mobile phase: acetonitrile/water with 0.1% TFA, gradient 30:70→95:5). This gave 125 mg (18% of theory) of the target compound.

LC-MS (Method 1) $R_t$=1.02 min; MS (ESIpos): m/z=390 (M+H)⁺

¹H NMR (400 MHz, DMSO-d₆): δ [ppm]=5.94 (s, 2H), 7.16 (t, 1H), 7.22-7.27 (m, 2H), 7.35-7.40 (m, 1H), 7.48 (dd, 1H), 7.79 (s br, 1H), 8.72 (dd, 1H), 8.78 (s br, 1H), 8.94 (dd, 1H).

Example 15

6-Cyclopentyl-3-[1-(2-fluorobenzyl)-1H-pyrazolo[3,4-b]pyridin-3-yl]-1,2,4-triazin-5-ol

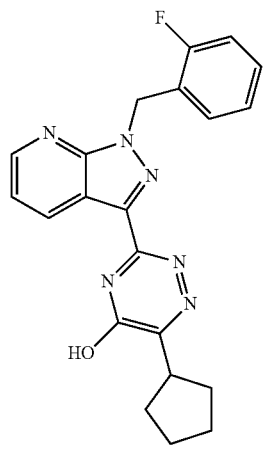 [SMILES: Oc1nc(-c2nn(Cc3ccccc3F)c3ncccc23)nnc1C1CCCC1]

1.197 g (7.035 mmol) of ethyl cyclopentyl(oxo)acetate in 15 ml of ethanol were initially introduced and heated to reflux. Then, 2.000 g (7.035 mmol) of 1-(2-fluorobenzyl)-1H-pyrazolo[3,4-d]pyrimidine-3-carboximidohydrazide suspended in 20 ml of ethanol were added and the mixture was heated under reflux overnight. After cooling, the mixture was concentrated and the residue was purified by preparative HPLC (mobile phase: acetonitrile/water with 0.1% TFA, ratio 45:55). This gave 749 mg of the target compound (26% of theory).

LC-MS (Method 2) $R_t$=1.10 min; MS (ESIpos): m/z=391 (M+H)⁺

¹H NMR (400 MHz, DMSO-d₆): δ [ppm]=1.60-1.78 (m, 6H), 1.91-1.98 (m, 2H), 5.90 (s, 2H), 7.15 (t, 1H), 7.22-7.28

(m, 2H), 7.35-7.40 (m, 1H), 7.48-7.51 (m, 1H), 8.73 (s, 1H), 8.75 (dd, 1H), 14.25 (s br, 1H).

Example 16

6-Cyclopentyl-3-[1-(2-fluorobenzyl)-1H-pyrazolo[3,4-b]pyridin-3-yl]-1,2,4-triazine-5-amine

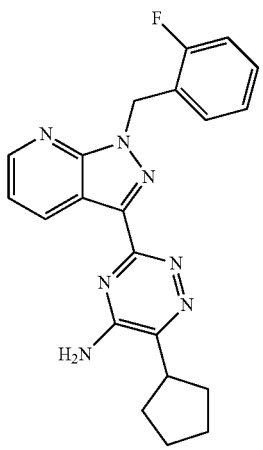 [SMILES: Nc1nc(-c2nn(Cc3ccccc3F)c3ncccc23)nnc1C1CCCC1]

730 mg (1.870 mmol) of 6-cyclopentyl-3-[1-(2-fluorobenzyl)-1H-pyrazolo[3,4-b]pyridin-3-yl]-1,2,4-triazin-5-ol were admixed with 9 ml of phosphoryl chloride and stirred overnight at RT. The reaction mixture was diluted with 50 ml of dry acetonitrile and, with ice-cooling, stirred into 130 ml of concentrated aqueous ammonia solution (25% strength). Stirring was carried out for 48 h at RT and for 24 h at 50° C. After cooling, the acetonitrile was removed on a rotary evaporator, the precipitate was filtered off with suction and the filtercake was washed with a little water. The residue was purified by preparative HPLC (mobile phase: acetonitrile/water with 0.1% TFA, gradient 30:70→95:5). This gave 508 mg (70% of theory) of the target compound.

LC-MS (Method 1) Rt=0.90 min; MS (ESIpos): m/z=390 (M+H)+

$^1$H NMR (400 MHz, DMSO-d$_6$): δ [ppm]=1.62-1.88 (m, 6H), 2.01-2.09 (m, 2H), 3.36 (qint, 1H), 5.92 (s, 2H), 7.16 (t, 1H), 7.22-7.29 (m, 2H), 7.35-7.41 (m, 1H), 7.54 (dd, 1H), 8.76 (dd, 1H), 8.90 (dd, 1H).

Example 17

3-[1-(2-Fluorobenzyl)-1H-pyrazolo[3,4-b]pyridin-3-yl]-6-propyl-1,2,4-triazin-5-ol

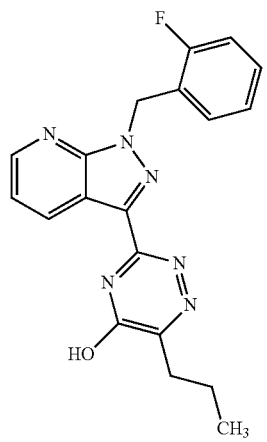 [SMILES: CCCc1nnc(-c2nn(Cc3ccccc3F)c3ncccc23)nc1O]

0.916 g (7.035 mmol) of methyl 2-oxopentanoate in 15 ml of ethanol were initially introduced and heated to reflux. Then, 2.000 g (7.035 mmol) of 1-(2-fluorobenzyl)-1H-pyrazolo[3,4-d]pyrimidine-3-carboximidohydrazide suspended in 20 ml of ethanol were added and the mixture was heated under reflux overnight. After cooling, the mixture was filtered off with suction, and the filtercake was washed with a little ethanol and dried under high vacuum. This gave 1.75 g of the target compound (purity 92%; 63% of theory).

LC-MS (Method 1) Rt=0.96 min; MS (ESIpos): m/z=365 (M+H)+

$^1$H NMR (400 MHz, DMSO-d$_6$): δ [ppm]=0.95 (t, 3H), 1.66 (sext, 2H), 2.60 (t, 2H), 5.90 (s, 2H), 7.15 (t, 1H), 7.22-7.27 (m, 2H), 7.35-7.40 (m, 1H), 7.50 (dd, 1H), 8.73 (s, 1H), 8.75 (dd, 1H), 14.27 (s br, 1H).

Example 18

3-[1-(2-Fluorobenzyl)-1H-pyrazolo[3,4-b]pyridin-3-yl]-6-propyl-1,2,4-triazine-5-amine

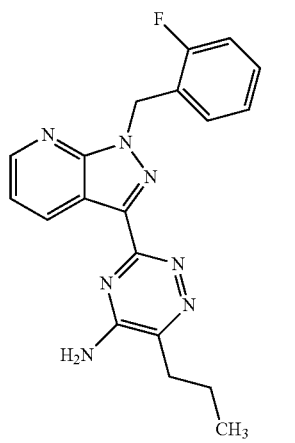 [SMILES: CCCc1nnc(-c2nn(Cc3ccccc3F)c3ncccc23)nc1N]

1.730 g (4.748 mmol) of 3-[1-(2-fluorobenzyl)-1H-pyrazolo[3,4-b]pyridin-3-yl]-6-propyl-1,2,4-triazin-5-ol were admixed with 23 ml of phosphoryl chloride and stirred overnight at RT. The reaction mixture was diluted with 100 ml of dry acetonitrile and, with ice-cooling, stirred into 330 ml of concentrated aqueous ammonia solution (25% strength). Stirring was carried out for 48 h at RT and for 24 h at 50° C. After cooling, the mixture was concentrated on a rotary evaporator, the residue was stirred with 200 ml of water and filtered off with suction and the filtercake was washed with a little water. The residue was purified by preparative HPLC (mobile phase: acetonitrile/water with 0.1% TFA, gradient 30:70→95:5). This gave 1.360 g (60% of theory) of the target compound.

LC-MS (Method 1) $R_t$=0.82 min; MS (ESIpos): m/z=364 (M+H)$^+$ $^1$H NMR (400 MHz, DMSO-d$_6$): δ [ppm]=1.00 (t, 3H), 1.72 (sext, 2H), 2.76 (t, 2H), 5.92 (s, 2H), 7.16 (t, 1H), 7.22-7.28 (m, 2H), 7.35-7.41 (m, 1H), 7.53 (dd, 1H), 8.76 (dd, 1H), 8.89 (dd, 1H).

Example 19

6-Ethyl-3-[1-(2-fluorobenzyl)-1H-pyrazolo[3,4-b]pyridin-3-yl]-1,2,4-triazin-5-ol

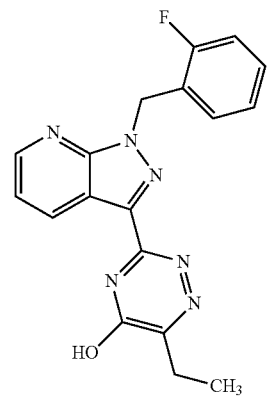 [SMILES: CCc1nnc(-c2nn(Cc3ccccc3F)c3ncccc23)nc1O]

0.817 g (7.035 mmol) of methyl 2-oxobutanoate in 15 ml of ethanol were initially introduced and heated to reflux. Then, 2.000 g (7.035 mmol) of 1-(2-fluorobenzyl)-1H-pyrazolo[3,4-d]pyrimidine-3-carboximidohydrazide suspended in 20 ml of ethanol were added and the mixture was heated under reflux overnight. After cooling, the mixture was filtered off with suction, and the filtercake was washed with a little ethanol and dried under high vacuum. This gave 1.83 g of the target compound (74% of theory).

LC-MS (Method 5) $R_t$=1.98 min; MS (ESIpos): m/z=351 (M+H)$^+$

¹H NMR (400 MHz, DMSO-d₆): δ [ppm]=1.17 (t, 3H), 2.66 (q, 2H), 5.90 (s, 2H), 7.15 (t, 1H), 7.22-7.27 (m, 2H), 7.35-7.41 (m, 1H), 7.50 (dd, 1H), 8.73 (s, 1H), 8.75 (d, 1H), 14.25 (s br, 1H).

Example 20

6-Ethyl-3-[1-(2-fluorobenzyl)-1H-pyrazolo[3,4-b]pyridin-3-yl]-1,2,4-triazine-5-amine

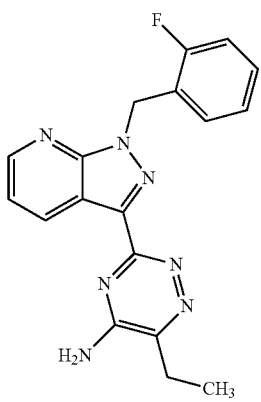 [SMILES: CCc1nnc(-c2nn(Cc3ccccc3F)c3ncccc23)nc1N]

1.800 g (5.138 mmol) of 6-ethyl-3-[1-(2-fluorobenzyl)-1H-pyrazolo[3,4-b]pyridin-3-yl]-1,2,4-triazin-5-ol were admixed with 25 ml of phosphoryl chloride and stirred overnight at RT. The reaction mixture was diluted with 100 ml of dry acetonitrile and, with ice-cooling, stirred into 375 ml of concentrated aqueous ammonia solution (25% strength). Stirring was carried out for 4 h at RT. Concentration on a rotary evaporator was carried out and the residue was partitioned between water and ethyl acetate. The organic phase was dried over sodium sulphate and concentrated on a rotary evaporator. The residue was purified by preparative HPLC (mobile phase: acetonitrile/water with 0.1% TFA, gradient 30:70→95:5). This gave 157 mg (8% of theory) of the target compound.

LC-MS (Method 1) $R_t$=0.81 min; MS (ESIpos): m/z=350 (M+H)⁺

¹H NMR (400 MHz, DMSO-d₆): δ [ppm]=1.26 (t, 3H), 2.80 (q, 2H), 5.92 (s, 2H), 7.16 (t, 1H), 7.22-7.29 (m, 2H), 7.35-7.41 (m, 1H), 7.54 (dd, 1H), 8.76 (dd, 1H), 8.89 (dd, 1H).

Example 21

3-[1-(2-Fluorobenzyl)-1H-pyrazolo[3,4-b]pyridin-3-yl]-6-isopropyl-1,2,4-triazin-5-ol

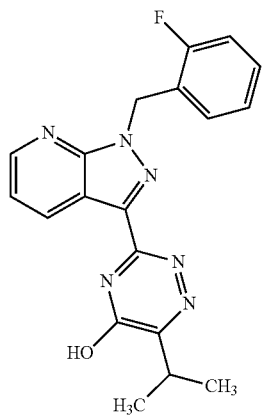 [SMILES: CC(C)c1nnc(-c2nn(Cc3ccccc3F)c3ncccc23)nc1O]

1.014 g (7.035 mmol) of ethyl 3-methyl-2-oxobutanoate in 15 ml of ethanol were initially introduced and heated to reflux. Then, 2.000 g (7.035 mmol) of 1-(2-fluorobenzyl)-1H-pyrazolo[3,4-d]pyrimidine-3-carboximidohydrazide suspended in 20 ml of ethanol were added and the mixture was heated under reflux overnight. After cooling, the mixture was filtered off with suction, and the filtercake was washed with a little ethanol and dried under high vacuum. This gave 918 mg of the target compound (36% of theory).

LC-MS (Method 1) $R_t$=1.01 min; MS (ESIpos): m/z=365 (M+H)⁺

¹H NMR (400 MHz, DMSO-d₆): δ [ppm]=1.20 (d, 6H), 3.22 (sept, 1H), 5.90 (s, 2H), 7.15 (t, 1H), 7.22-7.27 (m, 2H), 7.35-7.40 (m, 1H), 7.49-7.52 (m, 1H), 8.73 (s, 1H), 8.75 (dd, 1H), 14.30 (s br, 1H).

Example 22

3-[1-(2-Fluorobenzyl)-1H-pyrazolo[3,4-b]pyridin-3-yl]-6-isopropyl-1,2,4-triazine-5-amine

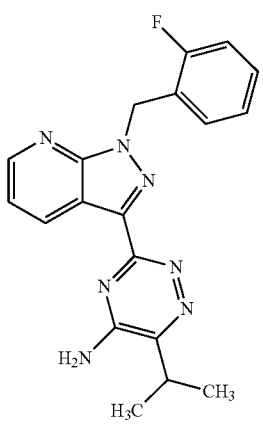 [SMILES: CC(C)c1nnc(-c2nn(Cc3ccccc3F)c3ncccc23)nc1N]

900 mg (5.138 mmol) of 3-[1-(2-fluorobenzyl)-1H-pyrazolo[3,4-b]pyridin-3-yl]-6-isopropyl-1,2,4-triazin-5-ol were admixed with 12 ml of phosphoryl chloride and stirred overnight at RT. The reaction mixture was diluted with 50 ml of dry acetonitrile and, with ice-cooling, stirred into 173 ml of concentrated aqueous ammonia solution (25% strength). The reaction mixture was stirred for 2 h at RT and for 6 h at 50° C. After cooling, concentration on a rotary evaporator was carried out.

The residue was partitioned between water and ethyl acetate. The organic phase was dried over sodium sulphate and concentrated on a rotary evaporator. The residue was stirred with diethyl ether, filtered off with suction and dried under high vacuum. This gave 266 mg (purity 92%, 27% of theory) of the target compound.

LC-MS (Method 2) $R_t$=0.82 min; MS (ESIpos): m/z=364 (M+H)⁺

¹H NMR (400 MHz, DMSO-d₆): δ [ppm]=1.28 (d, 6H), 3.24 (sept, 1H), 5.84 (s, 2H), 7.12-7.26 (m, 3H), 7.33-7.39 (m, 1H), 7.41 (dd, 1H), 8.66 (d, 1H), 8.91 (d, 1H).

Example 23

3-[1-(2-Fluorobenzyl)-1H-pyrazolo[3,4-b]pyridin-3-yl]-6-(1-fluoroethyl)-1,2,4-triazine-5-amine

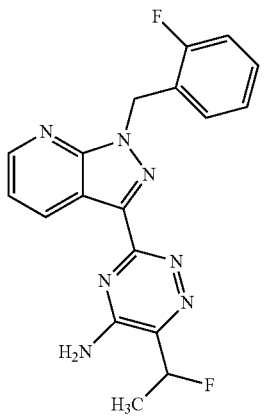 [SMILES: CC(F)c1nnc(-c2nn(Cc3ccccc3F)c3ncccc23)nc1N]

290 mg (purity 95%, 0.671 mmol) of 2-{5-amino-3-[1-(2-fluorobenzyl)-1H-pyrazolo[3,4-b]pyridin-3-yl]-1,2,4-triazin-6-yl}-2-fluoropropanamide were initially introduced in 2.6 ml of acetic acid and 2 drops of 1N hydrochloric acid were added. The mixture was stirred for 30 min at 100° C. in the microwave. After cooling, the reaction solution was admixed with ethyl acetate and washed with saturated sodium hydrogencarbonate solution. The organic phase was dried over sodium sulphate and concentrated. The residue was purified by preparative HPLC (mobile phase: acetonitrile/water, gradient 30:70→95:5). This gave 23 mg (purity 89%, 8% of theory) of the target compound.

LC-MS (Method 1) Rt=0.88 min; MS (ESIpos): m/z=368 (M+H)⁺

¹H NMR (400 MHz, DMSO-d₆): δ [ppm]=1.76 (dd, 3H), 5.86 (s, 2H), 6.03 (dq, 1H), 7.13-7.26 (m, 3H), 7.34-7.40 (m, 1H), 7.44 (dd, 1H), 7.50 (s br, 1H), 8.24 (s br, 1H), 8.69 (dd, 1H), 8.92 (dd, 1H).

B. Assessment of Pharmacological Efficacy

The pharmacological effect of the compounds according to the invention can be shown in the following assays:

B-1. Vasorelaxant Effect In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To produce a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. This is used to calculate the concentration needed to reduce the magnitude of the control value by 50% ($IC_{50}$ value). The standard administration volume is 5 µl; the DMSO content in the bath solution corresponds to 0.1%.

Representative $IC_{50}$ values for the compounds according to the invention are shown in the table below (Table 1):

TABLE 1

| Example No. | $IC_{50}$ [nM] |
|---|---|
| 11 | 2960 |
| 12 | 112 |
| 13 | 2630 |
| 14 | 52 |
| 15 | 1090 |
| 16 | 25 |
| 18 | 30 |
| 20 | 30 |
| 21 | 916 |
| 22 | 27 |
| 23 | 23 |

B-2. Effect on a Recombinant Guanylate Cyclase Reporter Cell Line

The cellular effect of the compounds according to the invention is determined using a recombinant guanylate cyclase reporter cell line, as described in F. Wunder et al., Anal. Biochem. 339, 104-112 (2005).

Representative values (MEC=minimum effective concentration) for the compounds according to the invention are shown in the table below (Table 2):

TABLE 2

| Example No. | MEC [µM] |
|---|---|
| 1 | 0.1 |
| 2 | 0.1 |
| 3 | 0.3 |
| 4 | 0.03 |
| 5 | 0.1 |
| 6 | 0.1 |
| 7 | 0.1 |
| 8 | 0.1 |
| 9 | 0.1 |
| 10 | 0.1 |
| 11 | 1.0 |
| 12 | 0.3 |
| 13 | 3.0 |
| 14 | 0.03 |
| 15 | 1.0 |
| 16 | 0.03 |
| 17 | 1.0 |
| 18 | 0.1 |
| 19 | 1.0 |
| 20 | 0.1 |
| 21 | 0.3 |
| 22 | 0.1 |
| 23 | 0.1 |

B-3. Radiotelemetric Measurement of Blood Pressure on Conscious Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed.

An antibiotic (Tardomyocel COMP, Bayer, 1 ml/kg s.c.) is administered postoperatively for prophylaxis of infection.

Substances and Solutions

Unless indicated otherwise, the substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight.

A solvent-treated group of animals is employed as control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9.00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed to be the time 2 hours before administration, and so the selected data set encompasses the period from 7.00 am on the day of the experiment to 9.00 am the following day.

The data are smoothed over a presettable time by determination of the average (15-minute average) and transferred as a text file to a storage medium. The measured values presorted and compressed in this way are transferred into Excel templates and tabulated. For each day of the experiment, the data obtained are stored in a dedicated file bearing the number of the experiment. Results and test protocols are filed in paper form sorted by numbers.

Literature

Klaus Witte, Kai Hu, Johanna Swiatek, Claudia Müssig, Georg Ertl and Bjorn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-4. Determination of Pharmacokinetic Parameters Following Intravenous and Oral Administration The pharmacokinetic parameters of the inventive compounds are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at −20° C. until further processing.

An internal standard (which may also be a chemically unrelated substance) is added to the samples of the inventive compounds, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by means of LC-MS/MS using $C_{18}$ reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half life), MRT (mean residence time) and CL (clearance), using a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min After centrifugation at 1000 g, the plasma concentration is measured (by means of LC-MS/MS; see above) and determined by calculating the ratio of the $c_{blood}/c_{plasma}$ value.

B-5. Metabolic Study

To determine the metabolic profile of the compounds according to the invention, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds according to the invention were incubated with a concentration of about 0.1-10 µM. To this end, stock solutions of the compounds according to the invention having a concentration of 0.01-1 mM in acetonitrile were prepared, and then pipetted with 1:100 dilution into the incubation mixture. Liver microsomes and recombinant enzymes were incubated at 37° C. in 50 mM potassium phosphate buffer pH 7.4 with and without NADPH-generating system consisting of 1 mM NADP$^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%) and the protein was centrifuged off at about 15 000×g. The samples thus stopped were either analysed directly or stored at −20° C. until analysis.

The analysis is effected by means of high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic assessment of the compound according to the invention in the incubation mixtures.

C. Working Examples of Pharmaceutical Compositions

The compounds according to the invention can be converted to pharmaceutical formulations as follows:

Tablet:

Composition:

100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% solution (w/w) of the PVP in water. The granules are dried and mixed with the magnesium stearate for 5 minutes. This mixture is pressed with a conventional tableting press (for tablet dimensions see above). The guide value used for the pressing is a pressing force of 15 kN.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

A single dose of 100 mg of the compound according to the invention corresponds to 10 ml of oral suspension.

Production:

The Rhodigel is suspended in ethanol and the compound according to the invention is added to the suspension. The water is added while stirring. The mixture is stirred for about 6 h until swelling of the Rhodigel is complete.

Solution which can be Administered Orally:

Composition:

500 mg of the compound according to the invention, 2.5 g of polysorbate and 97 g of polyethylene glycol 400. 20 g of oral solution correspond to a single dose of 100 mg of the compound according to the invention.

Production:

The compound according to the invention is suspended in the mixture of polyethylene glycol and polysorbate while stirring. The stirring operation is continued until dissolution of the compound according to the invention is complete.

i.v. Solution:

The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:

1. A compound of the formula (I)

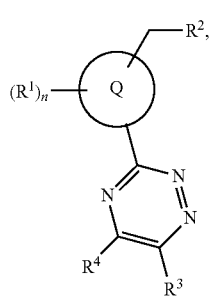

(I)

in which
the ring Q is a group of the formula

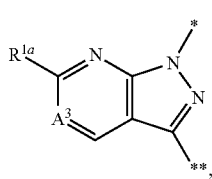

(a-1)

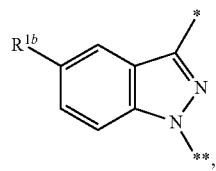

(b-1)

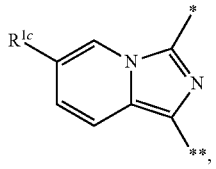

(c-1a)

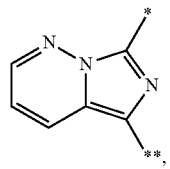

(c-1a)

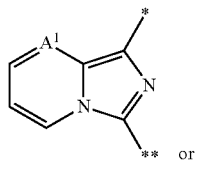

(d-1)

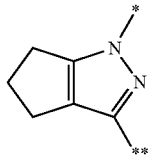

(l-1a)

where
* is the attachment site to —CH$_2$-R$^2$,
** is the attachment site to the triazine ring,
R$^{1a}$ is hydrogen or methyl,
R$^{1b}$ is hydrogen or fluorine,
R$^{1c}$ is hydrogen or chlorine,
A$^1$ is N or CH,
A$^3$ is N, CH or C—F,
R$^2$ is 3,3,3-trifluoroprop-1-yl, 2,2,3,3-tetrafluoroprop-1-yl, 2,2,3,3,3-pentafluoroprop-1-yl, phenyl or pyridyl,
where phenyl is substituted by 1 to 3 fluorine substituents,
and
where pyridyl may be substituted by 1 fluorine substituent,
R$^3$ is difluoromethyl, trifluoromethyl, (C$_1$-C$_6$)-alkyl, cyclopropyl, cyclobutyl, cyclopentyl, methylsulphonylamino, methoxycarbonylamino, phenyl, pyrazolyl, oxazolyl or pyridyl,
where (C$_1$-C$_6$)-alkyl may be substituted by 1 to 3 substituents independently of one another selected from the group consisting of fluorine, trifluoromethyl, cyclopropyl, cyclobutyl, cyclopentyl, difluoromethoxy, trifluoromethoxy, methoxy and ethoxy,
and
where phenyl, pyrazolyl, oxazolyl and pyridyl may be substituted by 1 or 2 substituents independently of one another selected from the group consisting of fluorine, chlorine, difluoromethyl, trifluoramethyl, methyl, ethyl, cyclopropyl, cyclobutyl, cyclopentyl, trifluoromethoxy, methoxy and ethoxy,
$R^4$ is hydroxy or amino,
or a salt thereof.
2. A compound of the formula (I)
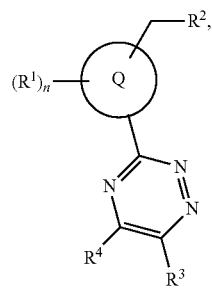
(I)
in which
the ring Q is a group of the formula
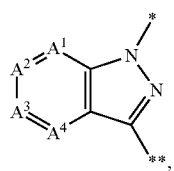
(a-1)
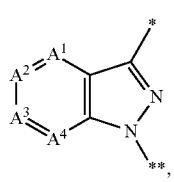
(b-1)
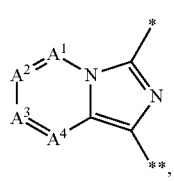
(c-1)
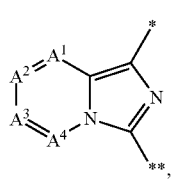
(d-1)
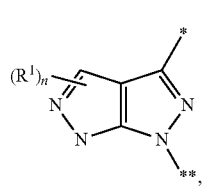
(e-1)
-continued
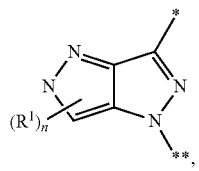
(f-1)
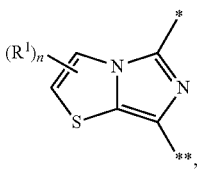
(g-1)
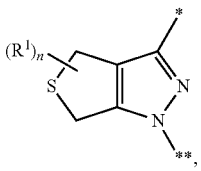
(h-1)
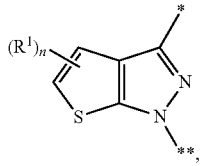
(i-1)
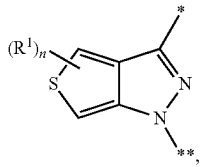
(j-1)
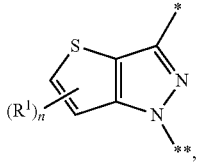
(k-1)
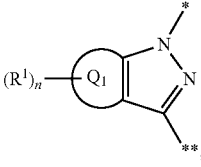
(l-1)
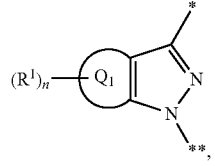
(m-1)
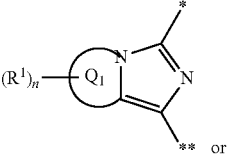
(n-1)
or -continued

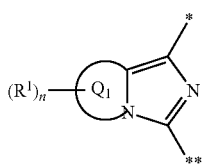
(o-1)

where
* is the attachment site to —CH$_2$—R$^2$,
** is the attachment site to the triazine ring,
the ring Q$_1$ together with the atoms to which it is bonded forms a 5- to 7-membered saturated or partly unsaturated carbocycle or a 5- to 7-membered saturated or partly unsaturated heterocycle,
A$^1$, A$^2$, A$^3$ and A$^4$ are each independently of one another N, CH or CR$^1$,
provided that not more than two of the A$^1$, A$^2$, A$^3$ and A$^4$ groups are N,
R$^1$ is fluorine, chlorine or methyl,
n is a number 0, 1 or 2,
R$^2$ is trifluoromethyl, 2,2,2-trifluoroethyl, 3,3,3-trifluoroprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl,
where phenyl is substituted by 1 to 3 fluorine substituents,
and
where cyclopropyl, cyclobutyl, cyclopentyl, cyclohexyl, pyridyl, pyrimidinyl, pyrazinyl and pyridazinyl may be substituted by 1 or 2 fluorine substituents,
R$^3$ is difluoromethyl, trifluoromethyl, (C$_1$-C$_6$)-alkyl, cyclopropyl, cyclobutyl, cyclopentyl, methylsulphonylamino, methoxycarbonylamino, phenyl, pyrazolyl, oxazolyl or pyridyl,
where (C$_1$-C$_6$)-alkyl may be substituted by 1 to 3 substituents independently of one another selected from the group consisting of fluorine, trifluoromethyl, cyclopropyl, cyclobutyl, cyclopentyl, difluoromethoxy, trifluoromethoxy, methoxy and ethoxy,
and
where phenyl, pyrazolyl, oxazolyl and pyridyl may be substituted by 1 or 2 substituents independently of one another selected from the group consisting of fluorine, chlorine, difluoromethyl, trifluoromethyl, methyl, ethyl, cyclopropyl, cyclobutyl, cyclopentyl, trifluoromethoxy, methoxy and ethoxy,
R$^4$ is hydroxy or amino,
or a salt thereof.

3. A process far preparing compounds of the formula (I) as defined in claim 2, comprising
[A] reacting a compound of the formula (II)

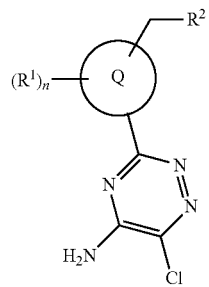
(II)

in which n, Q, R$^1$ and R$^2$ each have the meanings specified in claim 2, in an inert solvent in the presence of a suitable transition metal catalyst with a compound of the formula (III)

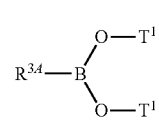
(III)

in which
R$^{3A}$ is phenyl, pyrazolyl, oxazolyl or pyridyl,
where phenyl and pyrazolyl, oxazolyl or pyridyl may be substituted by 1 or 2 substituents independently of one another selected from the group consisting of fluorine, chlorine, difluoromethyl, trifluoromethyl, methyl, ethyl, cyclopropyl, cyclobutyl, cyclopentyl, trifluoromethoxy, methoxy and ethoxy,
and
T$^1$ is hydrogen or (C$_1$-C$_4$)-alkyl, or both radicals together form a —C(CH$_3$)$_2$—C(CH$_3$)$_2$- bridge,
to give a compound of the formula (I-A)

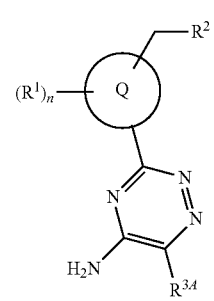
(I-A)

in which n, Q, R$^1$, R$^2$ and R$^{3A}$ each have the meanings specified above,
or
[B] reacting a compound of the formula (IV)

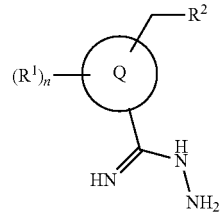
(IV)

in which n, Q, R$^1$ and R$^2$ each have the meanings specified in claim 2, in an inert solvent with a compound of the formula (V)

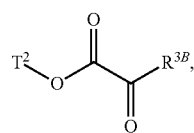

(V)

in which
R³ᴮ is difluoromethyl, trifluoromethyl, (C₁-C₆)-alkyl or cyclopropyl, cyclobutyl, cyclopentyl,
where (C₁-C₆)-alkyl may be substituted by 1 to 3 substituents independently of one another selected from the group consisting of fluorine, trifluoromethyl, cyclopropyl, cyclobutyl, cyclopentyl, difluoromethoxy, trifluoromethoxy, methoxy and ethoxy,
and
T² is (C₁-C₄)-alkyl,
to give a compound of the formula (I-B)

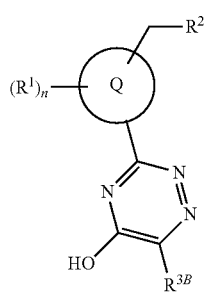

(I-B)

in which n, Q, R¹, R² and R³ᴮ each have the meanings specified above,
or

[C] reacting the compound of formula (I-B) with phosphoryl chloride to prepare a compound of the formula (VI)

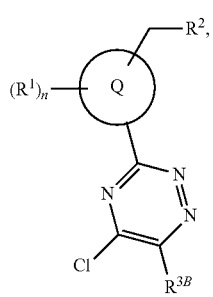

(VI)

in which n, Q, R¹, R² and R³ᴮ each have the meanings specified above, then reacting the compound of formula (VI) directly with ammonia to give a compound of the formula (I-C)

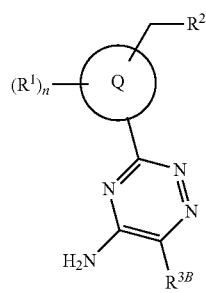

(I-C)

in which n, Q, R¹, R² and R³ᴮ each have the meanings specified above, wherein the resulting compounds of the formulae (I-A), I-B) and (I-C) are, optionally, converted with the appropriate (i) solvent and/or (ii) acid or base into a salt thereof.

4. A method of treatment of heart failure, angina pectoris, hypertension, pulmonary hypertension, ischaemias, vascular disorders, renal insufficiency, thromboembolic disorders, fibrotic diseases and arteriosclerosis comprising administering an effective amount of the compound of claim 2 to a human or animal in need thereof.

5. A pharmaceutical composition comprising the compound of claim 2 and an inert, nontoxic, pharmaceutically suitable excipient.

6. A pharmaceutical composition comprising the compound of claim 2 and an active compound selected from the group consisting of an organic nitrate, an NO donor, a cGMP-PDE inhibitor, an antithrombotic agent, a hypotensive agent and a lipid metabolism modifier.

7. A method of treatment of heart failure, angina pectoris, hypertension, pulmonary hypertension, ischaemias, vascular disorders, renal insufficiency, thromboembolic disorders, fibrotic disorders and arteriosclerosis comprising administering an effective amount of the pharmaceutical composition of claim 5 to a human or animal in need thereof.

* * * * *